US011859249B2

(12) United States Patent
Del Monaco et al.

(10) Patent No.: US 11,859,249 B2
(45) Date of Patent: Jan. 2, 2024

(54) METHOD AND KIT FOR THE GENERATION OF DNA LIBRARIES FOR MASSIVELY PARALLEL SEQUENCING

(71) Applicant: Menarini Silicon Biosystems S.p.A., Castel Maggiore (IT)

(72) Inventors: Valentina Del Monaco, Bologna (IT); Nicolò Manaresi, Bologna (IT); Genny Buson, Bologna (IT); Paola Tononi, Bologna (IT)

(73) Assignee: Menarini Silicon Biosystems S.p.A., Castel Maggiore (IT)

( * ) Notice: Subject to any disclaimer, the term of this patent is extended or adjusted under 35 U.S.C. 154(b) by 344 days.

(21) Appl. No.: 16/632,268

(22) PCT Filed: Jul. 20, 2018

(86) PCT No.: PCT/EP2018/069845
§ 371 (c)(1),
(2) Date: Jan. 17, 2020

(87) PCT Pub. No.: WO2019/016401
PCT Pub. Date: Jan. 24, 2019

(65) Prior Publication Data
US 2020/0362406 A1 Nov. 19, 2020

(30) Foreign Application Priority Data
Jul. 21, 2017 (EP) .................... 17182693

(51) Int. Cl.
*C12N 15/10* (2006.01)
*C12Q 1/68* (2018.01)
*C12Q 1/6874* (2018.01)

(52) U.S. Cl.
CPC ....... *C12Q 1/6874* (2013.01); *C12N 15/1093* (2013.01); *C12Q 2600/16* (2013.01)

(58) Field of Classification Search
CPC .................... C12N 15/1093; C12Q 1/6874
See application file for complete search history.

(56) References Cited

U.S. PATENT DOCUMENTS

2011/0319299 A1* 12/2011 Osborne et al. ............... 506/26
2019/0119008 A1 4/2019 Berroa Garcia

FOREIGN PATENT DOCUMENTS

CN 105359151 A 2/2016
KR 20160115913 A 10/2016
(Continued)

OTHER PUBLICATIONS

Klein et al. "Comparative genomic hybridization loss of heterozygosity, and DNA sequence analysis of single cells" Proc. Natl. Acad. Sci. USA, vol. 96, No. 8, Apr. 13, 1999, pp. 4494-4499 (Year: 1999).*

(Continued)

*Primary Examiner* — Aaron A Priest
*Assistant Examiner* — Randi Lynn Beil
(74) *Attorney, Agent, or Firm* — MARSHALL, GERSTEIN & BORUN LLP

(57) ABSTRACT

There is disclosed a method of generating a massively parallel sequencing library comprising the steps of: a) providing a primary WGA DNA library (pWGAlib), including fragments comprising a WGA library universal sequence adapter; b) performing a single PCR cycle on the pWGAlib using a first primer (1PR) comprising from 5' to 3' a first sequencing adapter (1PR5SA) and a first primer 3' section (1PR3S) hybridizing to the reverse complementary of the WGA library universal sequence adapter; c) performing a single PCR cycle on the on the product of step b) using a second primer (2PR) comprising from 5' to 3' a second sequencing adapter (2PR5SA) different from the 1PR5SA, and a second primer 3' section (2PR3S) hybridizing to the WGA library universal sequence adapter reverse comple- (Continued)

mentary; d) amplifying by PCR the product of step c) using a third primer comprising the 1PR5SA and a fourth primer comprising 2PR5SA.

8 Claims, 10 Drawing Sheets

Specification includes a Sequence Listing.

(56) References Cited

FOREIGN PATENT DOCUMENTS

| | | | |
|---|---|---|---|
| KR | 101678962 B1 | 12/2016 | |
| KR | 20170064260 A | 6/2017 | |
| WO | WO-00/17390 A1 | 3/2000 | |
| WO | WO-2012054873 A2 * | 4/2012 | ............. C12Q 1/683 |
| WO | WO 2012/166425 A2 * | 12/2012 | |
| WO | WO-2014/039556 A1 | 3/2014 | |
| WO | WO 2014/068519 A1 * | 5/2014 | |
| WO | WO-2014/071361 A1 | 5/2014 | |
| WO | WO-2014138153 A1 | 9/2014 | |
| WO | WO-2015083121 A1 | 6/2015 | |
| WO | WO-2015/148219 A1 | 10/2015 | |
| WO | WO-2016/195382 A1 | 12/2016 | |
| WO | WO-2017/178665 A1 | 10/2017 | |

OTHER PUBLICATIONS

Machine translation of WO 2016/195382 A1 (Bang et al.) downloaded Apr. 6, 2022 from https://patents.google.com/patent/WO2016195382A1/en?oq=WO+2016%2f195382 (Year: 2016).*

International Search Report and Written Opinion for Corresponding International Application No. PCT/EP2018/069845, dated Sep. 13, 2018.

Binder et al., "A New Workflow for Whole-Genome Sequencing of Single Human Cells" Human Mutation, 35(10) 1260-1270 (Aug. 2014).

Baslan et al., Optimizing sparse sequencing of single cells for highly multiplex copy number profiling, Genome Res., 25(5):714-24 (Apr. 2015).

Zong et al., "Genome-Wide Detection of Single-Nucleotide and Copy-Number Variations of a Single Human Cell", Science, 338(6114), 1622-1626, (Dec. 2012).

Gawad et al., "Single-Cell genome sequencing: current state of the science", Nature Reviews Genetics, 17(3), 175-188, (Jan. 2016).

Office Action issued in Israeli Patent Application No. 272039, dated Dec. 12, 2022.

Office Action, Japanese Patent Application No. 2020-502308, dated Aug. 9, 2022.

Japanese Patent Application No. 2020-502308, Summary of Decision of Final Rejection, dated Mar. 7, 2023.

Chinese Patent Application No. 2018800491442, First Office Action, dated Feb. 28, 2023.

* cited by examiner

METHOD AND KIT FOR THE GENERATION OF DNA LIBRARIES FOR MASSIVELY PARALLEL SEQUENCING

CROSS-REFERENCE TO RELATED APPLICATIONS

The present application is the U.S. national phase of International Patent Application No. PCT/EP2018/069845 filed Jul. 20, 2018, which claims priority from European Patent Application No. 17182693.6 filed on Jul. 21, 2017. The respective disclosures of which are incorporated herein by reference in their entireties.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "55254_Seqlisting.txt." The Sequence Listing was created on Jan. 17, 2020, and is 20,630 bytes in size. The subject matter of the Sequence Listing is incorporated herein in its entirety by reference.

TECHNICAL FIELD OF THE INVENTION

The present invention relates to a method and a kit to generate a massively parallel sequencing library for Whole Genome Sequencing from Whole Genome Amplification products (WGA). In particular, the method can advantageously be applied to Deterministic Restriction-Site, Whole Genome Amplification (DRS-WGA) DNA products.

The library can advantageously be used for low-pass whole-genome sequencing and genome-wide copy-number profiling.

PRIOR ART

With single cells it is useful to carry out a Whole Genome Amplification (WGA) for obtaining more DNA in order to simplify and/or make it possible to carry out different types of genetic analyses, including sequencing, SNP detection etc.

WGA with a LM-PCR based on a Deterministic Restriction Site (as described in e.g. WO/2000/017390) is known from the art (herein below referred to simply as DRS-WGA). A LM-PCR based, DRS-WGA commercial kit (Ampli1™ WGA kit, Menarini Silicon Biosystems) has been used in Hodgkinson C. L. et al., *Tumorigenicity and genetic profiling of circulating tumor cells in small-cell lung cancer*, Nature Medicine 20, 897-903 (2014). In this work, a Copy-Number Analysis by low-pass whole genome sequencing on single-cell WGA material was performed. However, for the standard workflow used in this paper, the creation of Illumina libraries required several steps, which included i) digestion of WGA adapters, ii) DNA fragmentation, and standard Illumina workflow steps such as iii) EndRepair iv) A-Tailing v) barcoded adapter ligation, plus the usual steps of vi) sample pooling of barcoded NGS libraries and vii) sequencing. As shown in the aforementioned article (FIG. 5b), WBC did present few presumably false-positive copy-number calls, although CTCs in general displayed many more aberrations.

Ampli1™ WGA is compatible with array Comparative Genomic Hybridization (aCGH); indeed several groups (Moehlendick B, et al. (2013) *A Robust Method to Analyze Copy Number Alterations of Less than* 100 *kb in Single Cells Using Oligonucleotide Array CGH*. PLoS ONE 8(6): e67031; Czyz Z T, et al (2014) *Reliable Single Cell Array CGH for Clinical Samples*. PLoS ONE 9(1): e85907) showed that it is suitable for high-resolution copy number analysis. However, aCGH technique is expensive and labor intensive, so that different methods such as low-pass whole-genome sequencing (LPWGS) for detection of somatic Copy-Number Alterations (CNA) may be desirable.

Although the DRS-WGA provides best results in terms of uniform and balanced amplification, current protocols based on aCGH or metaphase CGH are laborious and/or expensive. Low-pass whole-genome sequencing has been proposed as a high-throughput method to analyze several samples with higher processivity and lower cost than aCGH. However, known methods for the generation of a massively parallel sequencing library for WGA products (such as DRS-WGA) still require protocols including several enzymatic steps and reactions.

It would be desirable to have a more streamlined method, combining the reproducibility and quality of DRS-WGA with the capability to analyze genome-wide Copy-Number Variants (CNVs). In addition, determining a whole-genome copy number profile also from minute amount of cells, FFPE or tissue biopsies would be desirable.

PCT/EP2017/059075 in the name of the present applicant discloses a method for generating a massively parallel sequencing library—also referred to as an NGS (next generation sequencing) library—starting from a WGA product in a streamlined way.

The method involves amplifying the primary WGA DNA library with two primers, each of which includes a different sequencing adapter at the 5' end that will allow sequencing on a specific sequencing platform. The sequencing platforms that can be used are e.g. the Ion-Torrent platform or the Illumina platform.

When using certain sequencing platforms, e.g. the Illumina platform, it is particularly advantageous to select library fragments including the two different sequencing adapters (in the case of Illumina: P5 and P7) on the opposite ends of the fragment. These fragments will be referred to as "heteroadapter fragments". In order to do this, one of the embodiments disclosed in the above mentioned application provides that one of the two primers for amplifying the primary WGA DNA library is biotinylated at the 5' end. FIG. 1 summarizes this embodiment. Once the primary WGA DNA library has been amplified with the two primers, the fragments are selected by streptavidin beads. Fragments harboring the same sequencing adapters on both ends (hereinafter referred to as "homoadapter fragments") are either eluted (if not biotinylated) or remain bound to the streptavidin beads (if biotinylated on both ends), whereas ssDNA heteroadapter fragments (harboring different sequencing adapters at the two ends) are denatured and eluted so as to be selected.

The selection by biotinylated primers has some weaknesses. In particular, it leads to a single strand DNA library which is more difficult to quantify and less preferred for storage. In addition, for Illumina sequencing workflows the use of a double strand DNA library is preferable. This issue can be addressed by performing a double strand synthesis or further amplification cycles using P5 and P7 primers, but of course this renders the method somewhat more complicated and does not allow a single-tube reaction. The design of a kit is consequently more complex, as it requires e.g. the use of specific buffers designed for the purpose.

SUMMARY OF THE INVENTION

It is therefore an object of the present invention to provide a method for generating a massively parallel sequencing library starting from a WGA product that overcomes the above mentioned issues.

Other objects of the present invention are to provide a method for low-pass whole genome sequencing and a method for genome-wide copy-number profiling starting from a WGA product, using the library preparation method according to the invention.

Further objects of the present invention are to provide a massively parallel sequencing library preparation kit and a low-pass whole genome sequencing kit for implementing the above mentioned methods.

BRIEF DESCRIPTION OF THE DRAWINGS

FIG. 6A shows copy number alterations (CNA) profiles of a NCI-H23 single cell, obtained with a Low-pass Whole Genome Sequencing method for IonTorrent (presented in PCT/EP2017/059075) and with the method according to the present invention for Illumina platforms. FIG. 6B shows NCI-H441 and WBC single-cells hierarchical clustering, based on CNAs profiles.

DEFINITIONS

Figure 1:
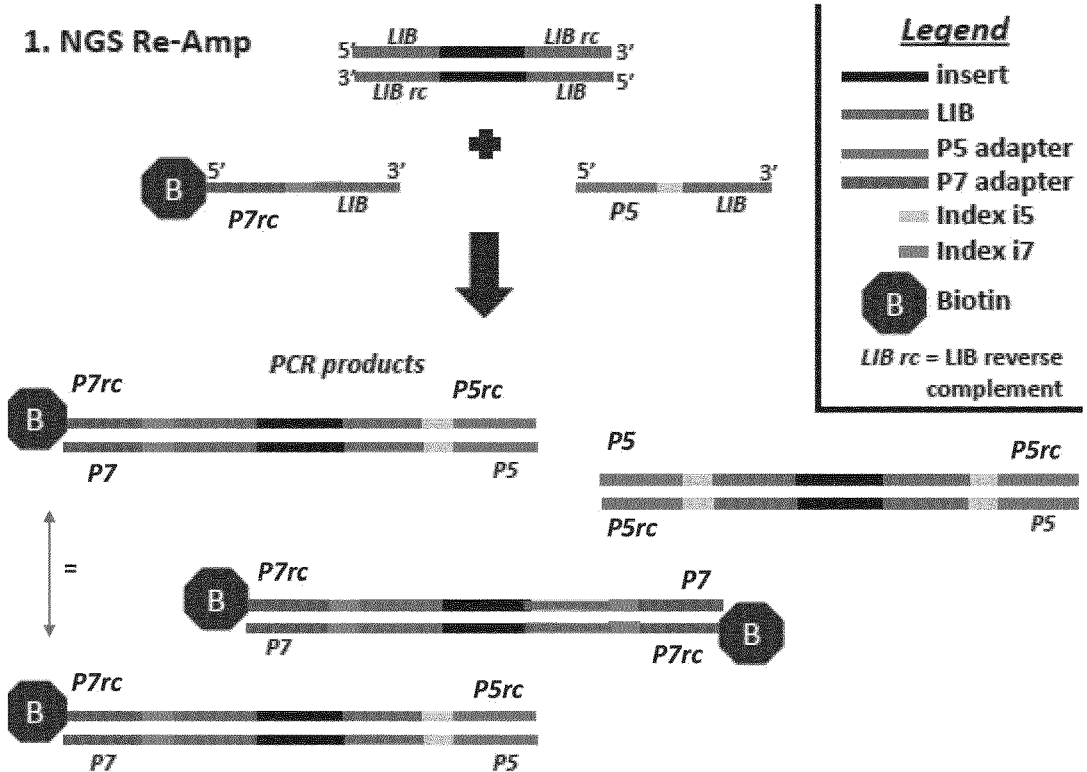
FIG. 1 shows a picture summarizing the steps of the method disclosed in PCT/EP2017/059075 by the applicant to select heteroadapter fragments.
Figure 1:
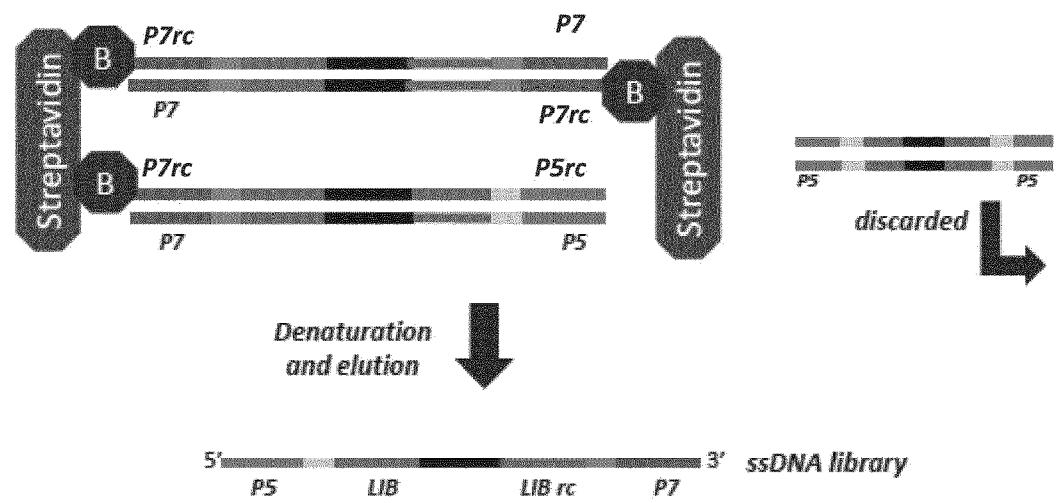

Unless defined otherwise, all technical and scientific terms used herein have the same meaning as commonly understood by one of ordinary skill in the art to which this invention pertains. Although many methods and materials similar or equivalent to those described herein may be used in the practice or testing of the present invention, preferred methods and materials are described below. Unless mentioned otherwise, the techniques described herein for use with the invention are standard methodologies well known to persons of ordinary skill in the art.

By the term "Original DNA" there is intended the genomic DNA (gDNA) prior to amplification with the DRS-WGA.

By the term "Adapter" or "WGA Adapter" or "WGA PCR Primer" or "WGA library universal sequence adapter" there is intended the additional oligonucleotide ligated to each fragment generated by the action of the restriction enzyme, in case of DRS-WGA, or the known polynucleotide sequence present at 5' section of each molecule of the WGA DNA library as a result of extension and PCR process, in case of MALBAC.

By the term "Copy Number Alteration (CNA)" there is intended a somatic change in copy-numbers of a genomic region, defined in general with respect to the same individual genome.

By the term "Copy Number Variation (CNV)" there is intended a germline variant in copy-numbers of a genomic region, defined in general with respect to a reference genome. Throughout the description CNA and CNV may be used interchangeably, as most of the reasoning can be applied to both situations. It should be intended that each of those terms refers to both situations, unless the contrary is specified.

By the term "massive-parallel sequencing" (MPS) or "next generation sequencing" (NGS) there is intended a method of sequencing DNA comprising the creation of a library of DNA molecules spatially and/or time separated, clonally sequenced (with or without prior clonal amplification). Examples include Illumina platform (Illumina Inc), Ion Torrent platform (ThermoFisher Scientific Inc), Pacific Biosciences platform, MinION (Oxford Nanopore Technologies Ltd).

By the term "Target sequence" there is intended a region of interest on the original DNA.

By the term "Primary WGA DNA library (pWGAlib)" there is intended a DNA library obtained from a WGA reaction.

By the term "Multiple Annealing and Looping Based Amplification Cycles (MALBAC)" there is intended a quasilinear whole genome amplification method (long et al., Genome-wide detection of single-nucleotide and copy-number variations of a single human cell, Science. 2012 Dec. 21; 338(6114):1622-6. doi: 10.1126/science.1229164). MALBAC primers have a 8 nucleotides 3' random sequence, to hybridize to the template, and a 27 nucleotides 5' common sequence (GTG AGT GAT GGT TGA GGT AGT GTG GAG). After first extension, semiamplicons are used as templates for another extension yielding a full amplicon which has complementary 5' and 3' ends. Following few cycles of quasi-linear amplification, full amplicon can be exponentially amplified with subsequent PCR cycles.

By the term "DNA library Purification" there is intended a process whereby the DNA library material is separated from unwanted reaction components such as enzymes, dNTPs, salts and/or other molecules which are not part of the desired DNA library. Example of DNA library purification processes are purification with paramagnetic bead-based technology (in the scientific literature and hereinafter for simplicity often referred to as "magnetic beads") such as Agencourt AMPure XP or solid-phase reversible immobilization (SPRI)-beads from Beckman Coulter or with spin column purification such as Amicon spin-columns from Merck Millipore. Another example of DNA library purification processes are purification with magnetic beads conjugated to oligonucleotide baits either directly or through protein-protein interactions such as streptavidin coated magnetic beads interacting with biotinylated oligonucleotides.

By the term "DNA library Selection" there is intended a process whereby either DNA library Purification or DNA library Size selection or both are carried out.

By the term "sequencing adapter (SA)" there is intended one or more molecules which are instrumental for sequencing the DNA insert. Each molecule may comprise none, one or more of the following: a polynucleotide sequence, a functional group. In particular, there is intended a polynucleotide sequence which is required to be present in a massively parallel sequencing library in order for the sequencer to correctly generate an output sequence, but which does not carry information, (as non-limiting examples: a polynucleotide sequence to hybridize a ssDNA to a flow-cell, in case of Illumina sequencing, or to an ion-sphere, in case of Ion Torrent sequencing, or a polynucleotide sequence required to initiate a sequencing-by-synthesis reaction).

By the term "sequencing barcode" there is intended a polynucleotide sequence which, when sequenced within one sequencer read, allows that read to be assigned to a specific sample associated with that barcode.

By the term "low-pass whole genome sequencing" there is intended a whole genome sequencing at a mean sequencing depth lower than 1.

By the term "mean sequencing depth" there is intended here, on a per-sample basis, the total of number of bases sequenced, mapped to the reference genome divided by the total reference genome size. The total number of bases sequenced and mapped can be approximated to the number of mapped reads times the average read length.

By "equalizing" there is intended the act of adjusting the concentration of one or more samples to make them equal.

By "normalizing" there is intended the act of adjusting the concentration of one or more samples to make them correspond to a desired proportion between them (equalizing being the special case where the proportion is 1). In the description, for the sake of simplicity, the terms normalizing and equalizing will be used indifferently as they are obviously conceptually identical.

DETAILED DESCRIPTION OF THE INVENTION

Figure 2A:
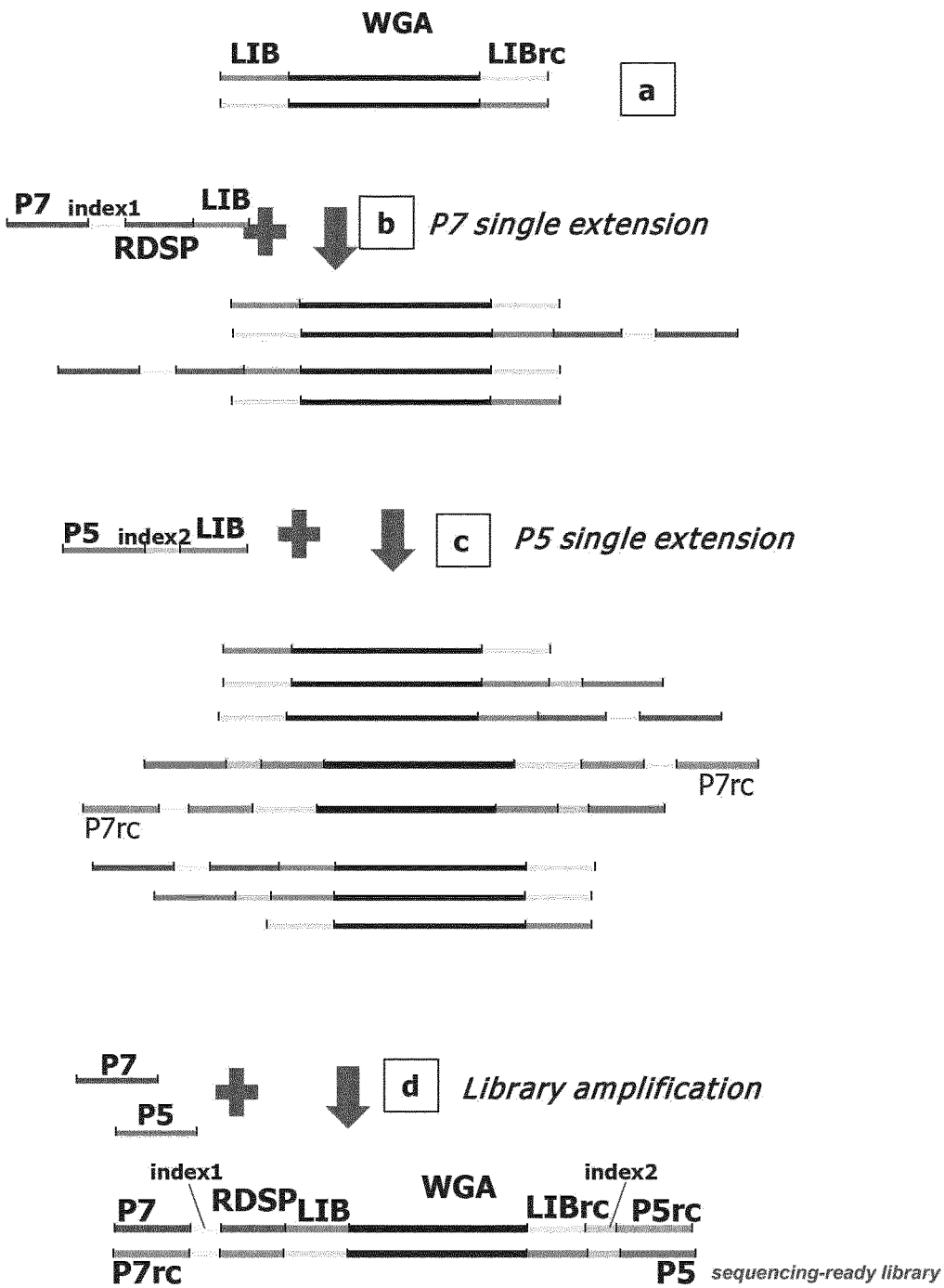
FIG. 2A shows a picture summarizing the steps of the method according to the present invention referring in particular to the situation in which the primary WGA DNA library is obtained by DRS-WGA. This is however not intended to limit the scope of the invention to this particular kind of WGA.

With reference to FIG. 2A, which exemplifies the case in which the primary WGA DNA library is obtained by DRS-WGA and the sequencing platform is the Illumina platform, the method of generating a massively parallel sequencing library according to the present invention comprises the following steps.

Figure 2B:
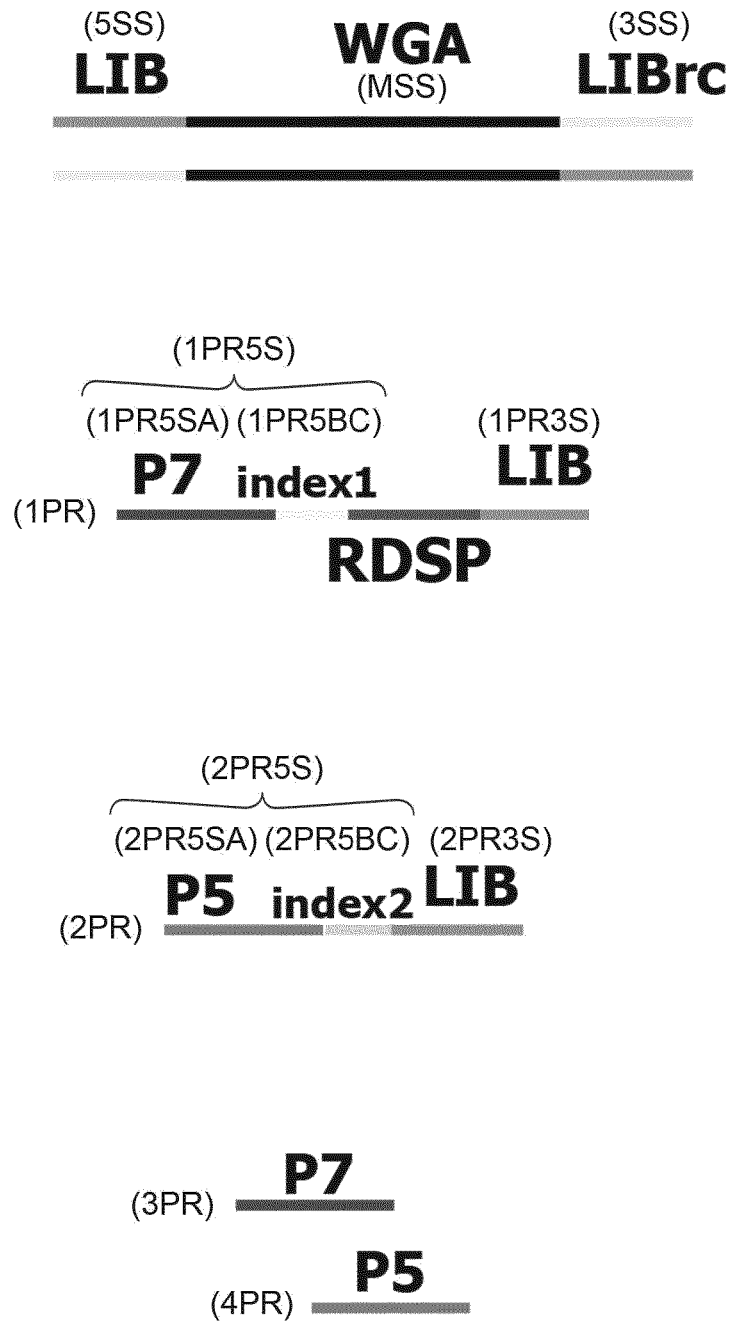
FIG. 2B shows the structure of the primary WGA DNA library and of the four primers used in the method according to the invention as shown in FIG. 2A. The acronyms used in the claims and description for the different segments of the primary WGA DNA library and of the four primers are also shown in parenthesis.
Figure 3A:
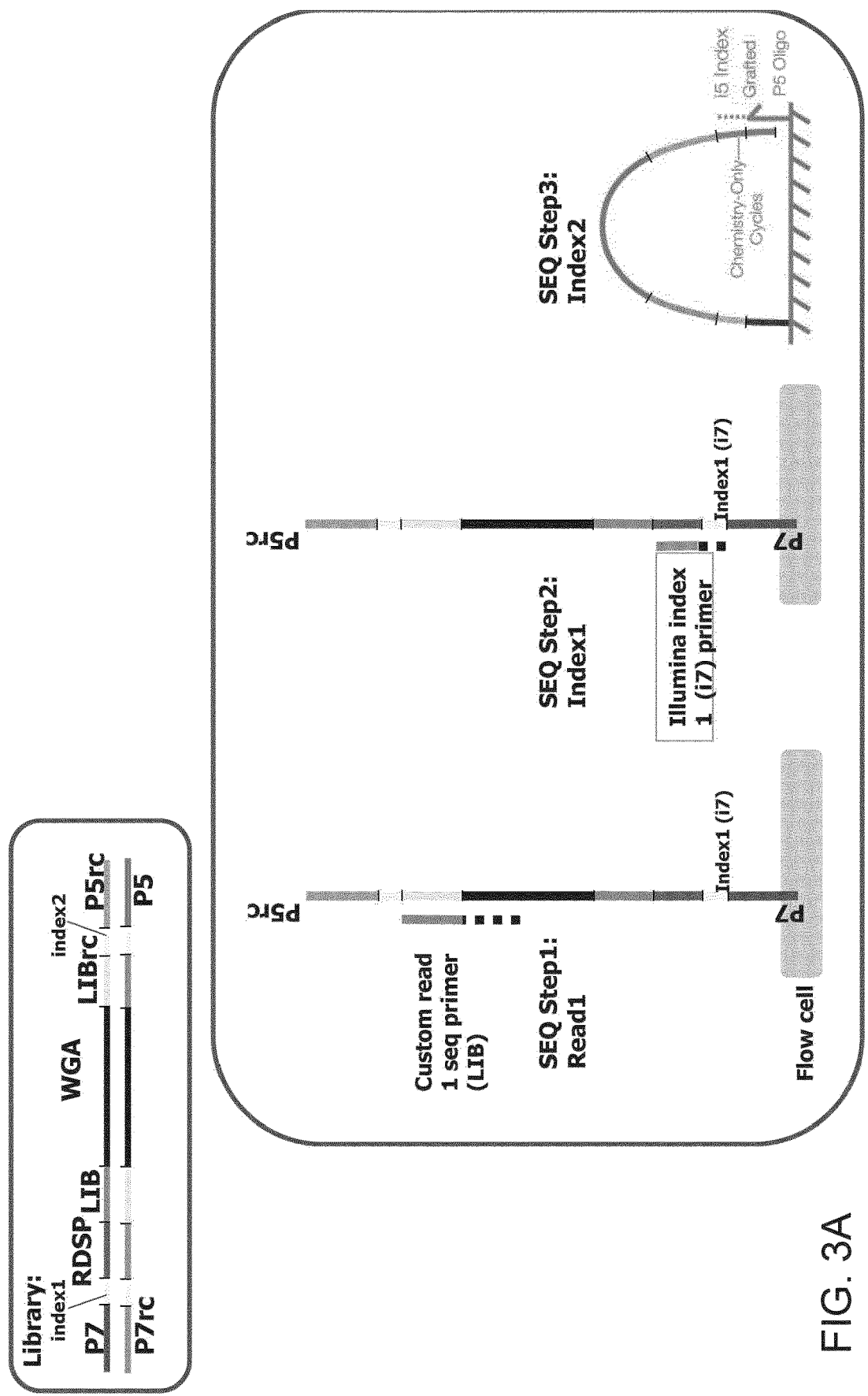
FIG. 3A shows a picture of dual index sequencing on MiSeq, HiSeq 2000/2500 and 1000/1500 with one custom sequencing primer according to the invention.
Figure 3B:
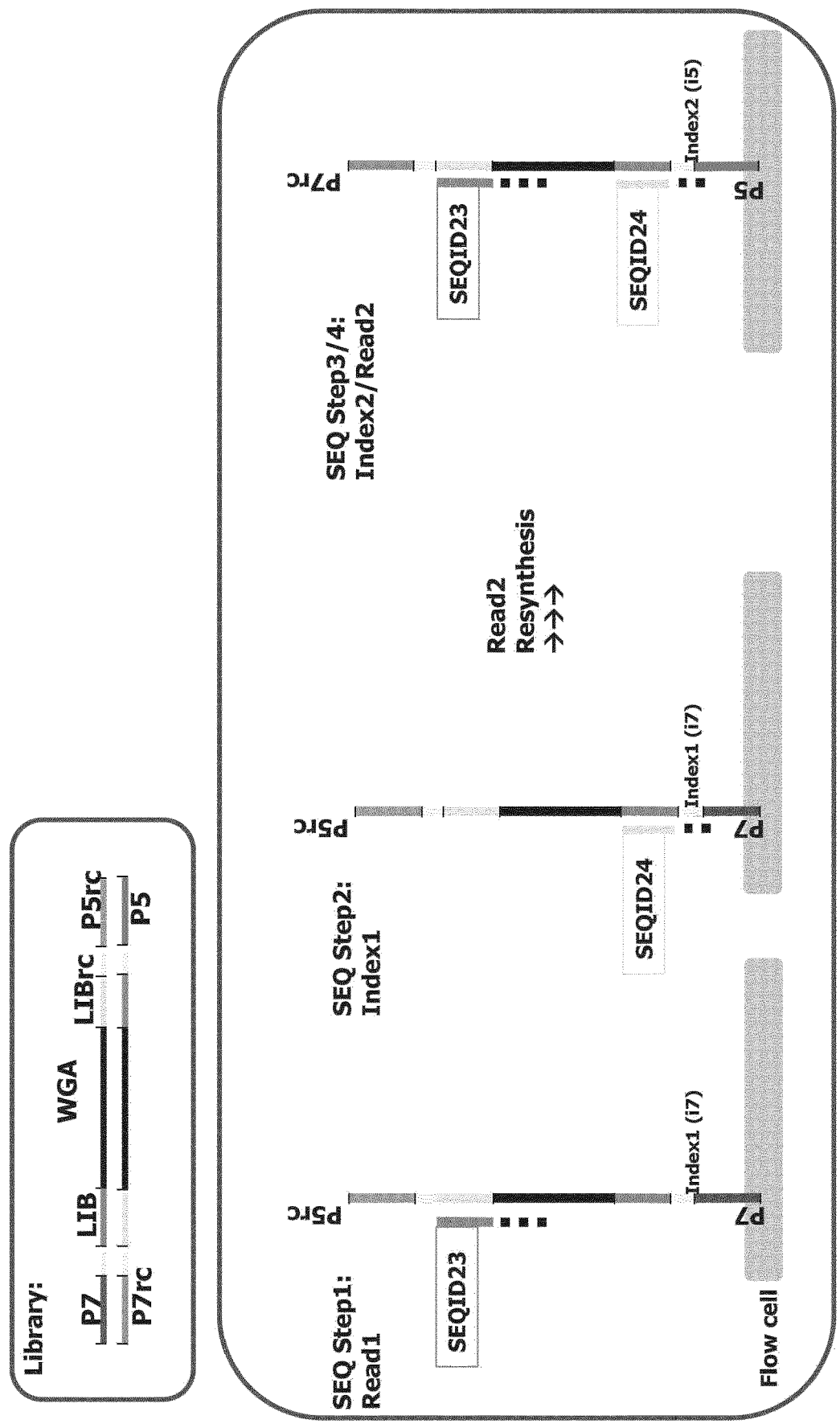
FIG. 3B shows a picture of dual index sequencing on MiniSeq, NextSeq, HiSeq 3000/4000 Illumina sequencing platforms, with two custom sequencing primers according to the invention.

In step a, there is provided a primary WGA DNA library (pWGAlib), which includes fragments comprising a known 5' sequence section (5SS), a middle sequence section (MSS), and a known 3' sequence section (3SS) reverse complementary to the known 5' sequence section. The known 5' sequence section (5SS) comprises a WGA library universal sequence adapter. The middle sequence section (MSS) comprises at least an insert section (IS), corresponding to a DNA sequence of the original unamplified DNA prior to WGA. The middle sequence section (MSS) optionally comprises, in addition to the insert section (IS), a flanking 5' intermediate section (F5) and/or a flanking 3' intermediate section (F3) (for example when the primary WGA DNA library is generated by MALBAC or by DRS-WGA according to the teachings of WO 2015/118077). In FIGS. 2A and 2B, the known 5' sequence section (5SS) corresponds to the LIB sequence (SEQ ID NO:50) specific for the DRS-WGA, and the known 3' sequence section (3SS) is the reverse complementary of the LIB sequence (LIBrc).

In step b, a single PCR cycle is performed on the primary WGA DNA library using at least one first primer (1PR), which comprises at least a first primer 5' section (1PR5S) and a first primer 3' section (1PR3S). The first primer 5' section (1PR5S) comprises at least one first sequencing adapter (1PR5SA). The first primer 3' section (1PR3S) hybridizes to the known 3' sequence section (3SS). The result of the single PCR cycle of step b is a first primer extended WGA DNA library.

A single PCR cycle includes a double strand DNA denaturation step, a primer annealing step and an annealed primer extension step. A preferred embodiment includes a denaturation step of 30 seconds at 95° C., an annealing step of 30 seconds at 62° C., and an extension step of 3 minutes at 72° C.

The first primer (1PR) preferably further comprises at least one read sequencing primer sequence (1PRSEQ) in 3' position of the first primer 5' section (1PR5S) and in 5' position of the first primer 3' section (1PR3S).

The first primer (1PR) preferably has a sequence selected from the group consisting of SEQ ID NO:1 to SEQ ID NO:12.

After step b, it is necessary to prevent that the first primer (1PR) polymerizes other primary WGA products or first primer extended WGA DNA library fragments. In a preferred embodiment the first primer extended WGA DNA library is purified after step b. This purification is preferably carried out with SPRIselect beads (Beckman Coulter).

In step c, a single PCR cycle is performed on the first primer extended WGA DNA library, using at least one second primer (2PR) comprising a second primer 5' section (2PR5S) and a second primer 3' section (2PR3S). The second primer 5' section (2PR5S) comprises at least one second sequencing adapter (2PR5SA) different from the at least one first sequencing adapter (1PR5SA). The second primer 3' section (2PR3S) hybridizes to the known 3' sequence section (3SS).

The result of the single PCR cycle of step c is a first and second primer extended WGA DNA library.

A single PCR cycle includes a double strand DNA denaturation step, a primer annealing step and an annealed primer extension step. A preferred embodiment includes a denaturation step of 30 seconds at 95° C., an annealing step of 30 seconds at 60° C., and an extension step of 3 minutes at 72° C.

The second primer (2PR) preferably has a sequence selected from the group consisting of SEQ ID NO:13 to SEQ ID NO:20.

After step c, the first and second primer extended WGA DNA library is purified, preferably with 2.5M NaCl PEG 20% solution.

In step d, the first and second primer extended WGA DNA library is amplified by using at least one third primer (3PR) comprising the first sequencing adapter (1PR5SA) and at least one fourth primer (4PR) comprising the second sequencing adapter (2PR5SA). The result of the PCR amplification of step d is an amplified first and second primer extended WGA DNA library. The yield of this amplification step in terms of DNA library is sufficient to carry out sequencing thereon.

After step d, the amplified first and second primer extended WGA DNA library is purified, preferably with 2.5M NaCl PEG 20% solution.

The third primer (3PR) preferably has sequence SEQ ID NO:22 and the fourth primer (4PR) preferably has sequence SEQ ID NO:21.

The first primer 5' section (1PR5S) of the first primer (1PR) preferably further comprises at least one first sequencing barcode (1PR5BC) in 3' position of the at least one first sequencing adapter (1PR5SA) and in 5' position of the first primer 3' section (1PR3S). The second primer 5' section (2PR5S) of the second primer (2PR) preferably further comprises at least one second sequencing barcode (2PR5BC), in 3' position of the at least one second sequencing adapter (2PR5SA) and in 5' position of the second primer 3' section (2PR3S). This allows for greater multiplexing. In particular, if SEQ ID NO:1 to SEQ ID NO:12 are used as first primer (1PR), each primer containing a different barcode, and SEQ ID NO:13 to SEQ ID NO:20 are used as second primer (2PR), each primer containing a different barcode, 96 combinations of barcodes can be obtained, leading to the analysis of 96 libraries.

The WGA library universal sequence adapter is preferably a DRS-WGA library universal sequence adapter or a MALBAC library universal sequence adapter, more preferably a DRS-WGA library universal sequence adapter.

The DRS-WGA library universal sequence adapter preferably has SEQ ID NO:50 and the MALBAC library universal sequence adapter preferably has SEQ ID NO:51.

The method for low-pass whole genome sequencing according to the present invention comprises the following steps.

First, there is provided a plurality of barcoded, massively-parallel sequencing libraries obtained according to the above disclosed method of generating a massively parallel sequencing library and samples obtained using different sequencing barcodes (BC) are pooled. Then the pooled library is sequenced.

The step of pooling samples using different sequencing barcodes (BC) further comprises the steps of quantitating the DNA in each of the barcoded, massively-parallel sequencing libraries, and of normalizing the amount of barcoded, massively-parallel sequencing libraries.

A massively parallel sequencing library preparation kit according to the present invention comprises at least one first primer (1PR), one second primer (2PR), one third primer (3PR) and one fourth primer (4PR). The structure of these primers has already been disclosed above.

In one preferred embodiment, in which the primary WGA DNA library is a DRS-WGA, the massively parallel sequencing library preparation kit comprises one or more primers selected from the group consisting of SEQ ID NO:1 to SEQ ID NO:12, one or more primers selected from the group consisting of SEQ ID NO:13 to SEQ ID NO:20, and primers SEQ ID NO:21 and SEQ ID NO:22.

In an alternative preferred embodiment, in which the primary WGA DNA library is a DRS-WGA, the massively parallel sequencing library preparation kit comprises one or more primers selected from the group consisting of SEQ ID NO:52 to SEQ ID NO:63, one or more primers selected from the group consisting of SEQ ID NO:13 to SEQ ID NO:20, and primers SEQ ID NO:21 and SEQ ID NO:22.

In an alternative preferred embodiment, in which the primary WGA DNA library is a MALBAC WGA, the massively parallel sequencing library preparation kit comprises one or more primers selected from the group consisting of SEQ ID NO:27 to SEQ ID NO:38, one or more primers selected from the group consisting of SEQ ID NO:39 to SEQ ID NO:46, and primers SEQ ID NO:21 and SEQ ID NO:22.

In an alternative preferred embodiment, in which the primary WGA DNA library is a MALBAC WGA, the massively parallel sequencing library preparation kit comprises one or more primers selected from the group consisting of SEQ ID NO:64 to SEQ ID NO:75, one or more primers selected from the group consisting of SEQ ID NO:39 to SEQ ID NO:46, and primers SEQ ID NO:21 and SEQ ID NO:22.

The low-pass whole genome sequencing kit according to one embodiment of the present invention comprises at least one primer selected from the group consisting of SEQ ID NO:1 to SEQ ID NO:12; at least one primer selected from the group consisting of SEQ ID NO:13 to SEQ ID NO:20; primers SEQ ID NO:21 and SEQ ID NO:22; and a custom sequencing primer of SEQ ID NO:23. The kit preferably also comprises a primer selected from the group consisting of SEQ ID NO:24, SEQ ID NO:25 and SEQ ID NO:26. In particular one of the latter primers is used with MiniSeq, NextSeq, HiSeq 3000/4000 Illumina sequencing platforms to read Index2. Additional explanation will be provided in the following. Among the three primers, SEQ ID NO:24 is particularly preferred.

In an alternative embodiment, the low-pass whole genome sequencing kit comprises at least one primer selected from the group consisting of SEQ ID NO:52 to SEQ ID NO:63; at least one primer selected from the group consisting of SEQ ID NO:13 to SEQ ID NO:20; primers SEQ ID NO:21 and SEQ ID NO:22; a custom sequencing primer of SEQ ID NO:23 and a custom index 2 primer selected from the group consisting of SEQ ID NO:24, SEQ ID NO:25 and SEQ ID NO:26.

The low-pass whole genome sequencing kit according to another embodiment of the present invention comprises at least one primer selected from the group consisting of SEQ ID NO:27 to SEQ ID NO:38; at least one primer selected from the group consisting of SEQ ID NO:39 to SEQ ID NO:46; primers SEQ ID NO:21 and SEQ ID NO:22; and primer of SEQ ID NO:47. The kit preferably also comprises SEQ ID NO:48. Even more preferably, the kit comprises a primer of SEQ ID NO:49.

In an alternative embodiment, the low-pass whole genome sequencing kit comprises at least one primer selected from the group consisting of SEQ ID NO:64 to SEQ ID NO:75; at least one primer selected from the group consisting of SEQ ID NO:39 to SEQ ID NO:46; primers SEQ ID NO:21 and SEQ ID NO:22; and primer of SEQ ID NO:47. The kit preferably also comprises SEQ ID NO:48. Even more preferably, the kit comprises a primer of SEQ ID NO:49.

The method for genome-wide copy number profiling according to the present invention comprises the steps of:
sequencing a DNA library developed using one of the above said sequencing library preparation kits;
analysing the sequencing read depth across different regions of the genome;

determining a copy-number value for the regions of the genome by comparing the number of reads in that region with respect to the number of reads expected in the same for a reference genome.

Protocol 1 for Low Pass Whole Genome Sequencing on Illumina Platforms

Deterministic-Restriction Site Whole Genome Amplification (DRS-WGA)

Single cell DNA was amplified using the Ampli1™ WGA Kit (Menarini Silicon Biosystems) according to the manufacturer's instructions. 5 µL of WGA-amplified DNA were diluted by the addition of 5 µL of Nuclease-Free Water and purified using SPRIselect beads (Beckman Coulter) system (ratio 1.8×). The DNA was eluted in 12.5 µL and quantified by dsDNA HS Assay on the Qubit® 2.0 Fluorometer.

P7 Single Extension

A single step of PCR extension was performed in a volume of 15 µl using Ampli1™ PCR Kit (Menarini Silicon Biosystems) and a LIB_IL_index D7xx (one of primers from SEQ ID NO:1 to SEQ ID NO:12). Each PCR reaction contained: 1.5 µL Ampli1™ PCR Reaction Buffer (10×), 3 µL of one primer LIB_IL_index D7xx within the following range: from SEQ ID NO:1 to SEQ ID NO:12 [2.5 µM], 0.51 µL Ampli1™ PCR dNTPs (10 mM), 0.37 µL BSA, 0.12 µL Ampli1™ PCR Taq Polymerase, WGA-purified DNA (from 10 to 75 ng) and Ampli1™ water to reach a final volume of 15 µL.

Applied Biosystems® 2720 Thermal Cycler was set as follows: 95° C. for 4 minutes, 1 cycle of 95° C. for 30 seconds, 62° C. for 30 seconds, 72° C. for 3 minutes.

SPRIselect Beads Clean-Up and P5 Single Extension

15 µL of Ampli1™ WGA-amplified from the previous step were purified using SPRIselect beads (Beckman Coulter) system (ratio 1.5×). The DNA was eluted in 15 µL of PCR reaction mix prepared as following: 1.54 Ampli1™ PCR Reaction Buffer (10×), 3 µL of one primer LIB_IL_index D5xx (one of primers from SEQ ID NO:13 to SEQ ID NO:20) [2.5 µM], 0.51 µL Ampli1™ PCR dNTPs (10 mM), 0.37 µL BSA, 0.12 µL Ampli1™ PCR Taq Polymerase and 9.5 µL Ampli1™ water. The P5 single extension PCR reaction was performed in the presence of beads.

Applied Biosystems® 2720 Thermal Cycler was set as follows: 95° C. for 4 minutes, 1 cycle of 95° C. for 30 seconds, 60° C. for 30 seconds, 72° C. for 3 minutes.

2.5M NaCl PEG 20% Solution Clean-Up and Library Amplification

15 µL of Ampli1 ™ WGA-amplified from the previous step were purified using 2.5M NaCl PEG 20% solution (ratio 1.5×). The DNA was eluted in 15 µL of PCR reaction mix prepared as following: 1.5 µL Ampli1™ PCR Reaction Buffer (10×), 1 µL of one primer adapter P5 (SEQ ID NO:21) and 1 µL of one primer adapter P7 (SEQ ID NO:22) (7.5 µM each), 0.51 µL Ampli1™ PCR dNTPs (10 mM), 0.37 µL BSA, 0.12 µL Ampli1™ PCR Taq Polymerase and 10.5 µL Ampli1™ water.

The library amplification PCR reaction was performed in the presence of beads.

Applied Biosystems® 2720 Thermal Cycler was set as follows: 95° C. for 4 minutes, 1 cycle of 95° C. for 30 seconds, 60° C. for 30 seconds, 72° C. for 2 minutes, 10 cycles of 95° C. for 30 seconds, 60° C. for 30 seconds, 72° C. for 2 minutes (extended by 20 seconds/cycle) and final extension at 72° C. for 7 minutes.

In a preferred embodiment, the cycles of 95° C. for 30 seconds, 60° C. for 30 seconds, 72° C. for 2 minutes can be extended to 12, to increase the library concentration of at least a 2(−4) factor by introducing 2 extra cycles during library amplification, thus increasing the total number of cycles from 11 to 13.

Final Library Clean-Up

The amplified library (containing Illumina sequencing adapter sequences) was finally purified using 2.5M NaCl PEG 20% solution (ratio 1.5×) and eluted in 15 µL of Ampli1™ water. The purified libraries were qualified by Agilent DNA 7500, DNA 1000 or DNA HS Kits on the 2100 Bioanalyzer® and quantified by dsDNA HS Assay on Qubit® 2.0 Fluorometer, in order to obtain an equimolar pool. Based on library average size (usually an average length of 700 bp is observed experimentally on DRS-WGA products obtained using Ampli1™ WGA kit—Menarini Silicon Biosystems), the library concentration generated by the quantification step can be converted to nM as known by those with ordinary skill in the art (for example 1 ng/µL=2.5 nM for 600 bp library average size, 1 ng/µL=2 nM for 700 bp library average size, 1 ng/µL=1.9 nM for 800 bp library average size)—see Illumina Technical Note: DNA Sequencing "Nextera® Library Validation and Cluster Density Optimization" Pub No. 770-2013-003.

As preferred alternative, the purified libraries were quantified by Quantitative real-time PCR (qPCR) methodology. The qPCR method accurately quantifies the functional libraries, in particular those fragments that have the correct adapter on each end (heteroadapter fragments), based on a standard curve generated from a control template dilutions. Sequencing on MiSeq sequencing system 4 nM of the pool was denatured 5 minutes with 0.1N NaOH. Denatured sample was then diluted with HT1 buffer (Illumina) to obtain a 20 µM denatured library. 600 µL of denatured library was loaded on MiSeq reagent cartridge (Illumina).

Single end reads of 150 bases or Paired end reads (75 PE) were generated using the v3 chemistry of the Illumina MiSeq.

Custom read1 sequencing primer (SEQ ID NO:23) was then diluted with HT1 to obtain a final concentration of 0.5 µM. 600 µL of diluted Custom read1 sequencing primer was loaded on MiSeq reagent cartridge (Illumina).

Sequencing on HiSeq 1000/1500 and 2000/2500 Systems 4 nM of the pool was denatured 5 minutes with 0.1N NaOH.

Single end reads of 100 bases or Paired end reads (100 PE) were generated using the v2 chemistry of the Illumina HiSeq, in Rapid run mode, or using the v4 chemistry of the Illumina HiSeq, in High Output run mode.

Custom read1 sequencing primer (SEQ ID NO:23) was then diluted with HT1 to obtain a final concentration of 0.5 µM.

Sequencing on NextSeq, HiSeq 3000 and 4000, NovaSeq Series and HiSeq X Ten Systems 4 nM of the pool was denatured 5 minutes with 0.1N NaOH.

Single end reads of 150 bases or Paired end reads (100 PE) were generated using specific chemistry for the Illumina platforms.

Custom read1 sequencing primer (SEQ ID NO:23) and Custom primer index 2A (i5) [LNA-5'] (SEQ ID NO:24) were then diluted with HT1 to obtain a final concentration of 0.5 µM.

The following table summarizes the sequences of the DRS-WGA compatible primers for all Illumina platforms (sequences in 5'→3' direction, 5' and 3' omitted):

TABLE 1

| SEQID | Name | Primer sequence |
|---|---|---|
| SEQID1 | LIB_IL_index D701 | CAAGCAGAAGACGGCATACGAGATCGAGTAATGTGACTGGAGTTCAGACGTGTGCTCTTCCGATCTAGTGGGATTCCTGCTGTCAGT |
| SEQID2 | LIB_IL_index D702 | CAAGCAGAAGACGGCATACGAGATTCTCCGGAGTGACTGGAGTTCAGACGTGTGCTCTTCCGATCTAGTGGGATTCCTGCTGTCAGT |
| SEQID3 | LIB_IL_index D703 | CAAGCAGAAGACGGCATACGAGATAATGAGCGGTGACTGGAGTTCAGACGTGTGCTCTTCCGATCTAGTGGGATTCCTGCTGTCAGT |
| SEQID4 | LIB_IL_index D704 | CAAGCAGAAGACGGCATACGAGATGGAATCTCGTGACTGGAGTTCAGACGTGTGCTCTTCCGATCTAGTGGGATTCCTGCTGTCAGT |
| SEQID5 | LIB_IL_index D705 | CAAGCAGAAGACGGCATACGAGATTTCTGAATGTGACTGGAGTTCAGACGTGTGCTCTTCCGATCTAGTGGGATTCCTGCTGTCAGT |
| SEQID6 | LIB_IL_index D706 | CAAGCAGAAGACGGCATACGAGATACGAATTCGTGACTGGAGTTCAGACGTGTGCTCTTCCGATCTAGTGGGATTCCTGCTGTCAGT |
| SEQID7 | LIB_IL_index D707 | CAAGCAGAAGACGGCATACGAGATAGCTTCAGGTGACTGGAGTTCAGACGTGTGCTCTTCCGATCTAGTGGGATTCCTGCTGTCAGT |
| SEQID8 | LIB_IL_index D708 | CAAGCAGAAGACGGCATACGAGATGCGCATTAGTGACTGGAGTTCAGACGTGTGCTCTTCCGATCTAGTGGGATTCCTGCTGTCAGT |
| SEQID9 | LIB_IL_index D709 | CAAGCAGAAGACGGCATACGAGATCATAGCCGGTGACTGGAGTTCAGACGTGTGCTCTTCCGATCTAGTGGGATTCCTGCTGTCAGT |
| SEQID10 | LIB_IL_index D710 | CAAGCAGAAGACGGCATACGAGATTTCGCGGAGTGACTGGAGTTCAGACGTGTGCTCTTCCGATCTAGTGGGATTCCTGCTGTCAGT |
| SEQID11 | LIB_IL_index D711 | CAAGCAGAAGACGGCATACGAGATGCGCGAGAGTGACTGGAGTTCAGACGTGTGCTCTTCCGATCTAGTGGGATTCCTGCTGTCAGT |
| SEQID12 | LIB_IL_index D712 | CAAGCAGAAGACGGCATACGAGATCTATCGCTGTGACTGGAGTTCAGACGTGTGCTCTTCCGATCTAGTGGGATTCCTGCTGTCAGT |
| SEQID13 | LIB_IL_index D501 | AATGATACGGCGACCACCGAGATCTACACTATAGCCTGCTCACCGAAGTGGGATTCCTGCTGTCAGTTAA |
| SEQID14 | LIB_IL_index D502 | AATGATACGGCGACCACCGAGATCTACACATAGAGGCGCTCACCGAAGTGGGATTCCTGCTGTCAGTTAA |
| SEQID15 | LIB_IL_index D503 | AATGATACGGCGACCACCGAGATCTACACCCTATCCTGCTCACCGAAGTGGGATTCCTGCTGTCAGTTAA |
| SEQID16 | LIB_IL_index D504 | AATGATACGGCGACCACCGAGATCTACACGGCTCTGAGCTCACCGAAGTGGGATTCCTGCTGTCAGTTAA |
| SEQID17 | LIB_IL_index D505 | AATGATACGGCGACCACCGAGATCTACACAGGCGAAGGCTCACCGAAGTGGGATTCCTGCTGTCAGTTAA |
| SEQID18 | LIB_IL_index D506 | AATGATACGGCGACCACCGAGATCTACACTAATCTTAGCTCACCGAAGTGGGATTCCTGCTGTCAGTTAA |
| SEQID19 | LIB_IL_index D507 | AATGATACGGCGACCACCGAGATCTACACCAGGACGTGCTCACCGAAGTGGGATTCCTGCTGTCAGTTAA |
| SEQID20 | LIB_IL_index D508 | AATGATACGGCGACCACCGAGATCTACACGTACTGACGCTCACCGAAGTGGGATTCCTGCTGTCAGTTAA |
| SEQID21 | Adapter P5 | AATGATACGGCGACCACCGAGAT |
| SEQID22 | Adapter P7 | CAAGCAGAAGACGGCATACGA |
| SEQID23 | Ampli1 ™ custom sequencing primer | GCTCACCGAAGTGGGATTCCTGCTGTCAGTTAA |
| SEQID24 | Custom primer index 2 A (i5) [LNA-5'] | A+CAGC+AGGAA+TCCCACTTCGGTGAGC |
| SEQID25 | Custom primer index 2 A (i5) [LNA-3'] | ACAGCAGGAATCCCACT+TCGG+TG+AGC |
| SEQID26 | Custom primer index 2(i5)[RNA] | TTrAArCTrGrACArGrCAGrGrArATCCrCrArCTArCGGrArGrAGC |

The following table summarizes the sequences of the MALBAC-WGA primers compatible for all Illumina platforms (sequences in 5'→3' direction, 5' and 3' omitted):

TABLE 2

| SEQID | Name | Primer sequence |
|---|---|---|
| SEQID27 | MAL_IL_index D701 | CAAGCAGAAGACGGCATACGAGATCGAGTAATGTGACTGGAGTTCAGACGTGTGCTCTTCCGATCTGTGAGTGATGGTTGAGGTAGTGTGGAG |
| SEQID28 | MAL_IL_index D702 | CAAGCAGAAGACGGCATACGAGATTCTCCGGAGTGACTGGAGTTCAGACGTGTGCTCTTCCGATCTGTGAGTGATGGTTGAGGTAGTGTGGAG |
| SEQID29 | MAL_IL_index D703 | CAAGCAGAAGACGGCATACGAGATAATGAGCGGTGACTGGAGTTCAGACGTGTGCTCTTCCGATCTGTGAGTGATGGTTGAGGTAGTGTGGAG |
| SEQID30 | MAL_IL_index D704 | CAAGCAGAAGACGGCATACGAGATGGAATCTCGTGACTGGAGTTCAGACGTGTGCTCTTCCGATCTGTGAGTGATGGTTGAGGTAGTGTGGAG |
| SEQID31 | MAL_IL_index D705 | CAAGCAGAAGACGGCATACGAGATTTCTGAATGTGACTGGAGTTCAGACGTGTGCTCTTCCGATCTGTGAGTGATGGTTGAGGTAGTGTGGAG |
| SEQID32 | MAL_IL_index D706 | CAAGCAGAAGACGGCATACGAGATACGAATTCGTGACTGGAGTTCAGACGTGTGCTCTTCCGATCTGTGAGTGATGGTTGAGGTAGTGTGGAG |
| SEQID33 | MAL_IL_index D707 | CAAGCAGAAGACGGCATACGAGATAGCTTCAGGTGACTGGAGTTCAGACGTGTGCTCTTCCGATCTGTGAGTGATGGTTGAGGTAGTGTGGAG |
| SEQID34 | MAL_IL_index D708 | CAAGCAGAAGACGGCATACGAGATGCGCATTAGTGACTGGAGTTCAGACGTGTGCTCTTCCGATCTGTGAGTGATGGTTGAGGTAGTGTGGAG |
| SEQID35 | MAL_IL_index D709 | CAAGCAGAAGACGGCATACGAGATCATAGCCGGTGACTGGAGTTCAGACGTGTGCTCTTCCGATCTGTGAGTGATGGTTGAGGTAGTGTGGAG |
| SEQID36 | MAL_IL_index D710 | CAAGCAGAAGACGGCATACGAGATTTCGCGGAGTGACTGGAGTTCAGACGTGTGCTCTTCCGATCTGTGAGTGATGGTTGAGGTAGTGTGGAG |
| SEQID37 | MAL_IL_index D711 | CAAGCAGAAGACGGCATACGAGATGCGCGAGAGTGACTGGAGTTCAGACGTGTGCTCTTCCGATCTGTGAGTGATGGTTGAGGTAGTGTGGAG |
| SEQID38 | MAL_IL_index D712 | CAAGCAGAAGACGGCATACGAGATCTATCGCTGTGACTGGAGTTCAGACGTGTGCTCTTCCGATCTGTGAGTGATGGTTGAGGTAGTGTGGAG |
| SEQID39 | MAL_IL_index D501 | AATGATACGGCGACCACCGAGATCTACACTATAGCCTGTGAGTGATGGTTGAGGTAGTGTGGAG |
| SEQID40 | MAL_IL_index D502 | AATGATACGGCGACCACCGAGATCTACACATAGAGGCGTGAGTGATGGTTGAGGTAGTGTGGAG |
| SEQID41 | MAL_IL_index D503 | AATGATACGGCGACCACCGAGATCTACACCCTATCCTGTGAGTGATGGTTGAGGTAGTGTGGAG |
| SEQID42 | MAL_IL_index D504 | AATGATACGGCGACCACCGAGATCTACACGGCTCTGAGTGAGTGATGGTTGAGGTAGTGTGGAG |
| SEQID43 | MAL_IL_index D505 | AATGATACGGCGACCACCGAGATCTACACAGGCGAAGGTGAGTGATGGTTGAGGTAGTGTGGAG |
| SEQID44 | MAL_IL_index D506 | AATGATACGGCGACCACCGAGATCTACACTAATCTTAGTGAGTGATGGTTGAGGTAGTGTGGAG |
| SEQID45 | MAL_IL_index D507 | AATGATACGGCGACCACCGAGATCTACACCAGGACGTGTGAGTGATGGTTGAGGTAGTGTGGAG |
| SEQID46 | MAL_IL_index D508 | AATGATACGGCGACCACCGAGATCTACACGTACTGACGTGAGTGATGGTTGAGGTAGTGTGGAG |
| SEQID47 | Custom Read 1 primer | GTGAGTGATGGTTGAGGTAGTGTGGAG |
| SEQID48 | Custom primer index 1 (i7) | CTCCACACTACCTCAACCATCACTCAC |
| SEQID49 | Custom primer reed 2 (optional) | GCTCACCGAAGTGGGATTCCTGCTGTCAGTTAA |

When DRS-WGA is used, the LIB reverse complementary is the target for the primers listed in TABLE 1, from SEQ ID NO:1 to SEQ ID NO:20, as shown in the FIGS. 2A and 2B. Furthermore, a custom read1 sequencing primer (SEQ ID NO:23) has been designed, because the final library lacks the target sequence of Illumina read1 sequencing primer. The custom read1 sequencing primer (SEQ ID NO:23) contains the LIB sequence and is complementary to the LIB reverse complementary sequence.

Noteworthy, in the sequencing setup it is possible to avoid to use a PhiX spike-in control (Illumina), because this method enables the construction of high-complexity libraries from our Ampli1™ WGA product input.

Furthermore, the sequencing run are preferably performed using the custom read1 sequencing primer (SEQ ID NO:23), the PhiX DNA library lacks the target sequence of custom read1 sequencing primer and for this reason the PhiX DNA will not be sequenced.

Moreover, the final library obtained by the method of the present invention does not have the canonical Illumina sequence-adapter used by MiniSeq, NextSeq, HiSeq 3000 and 4000 Illumina systems to read the index 2 (i5).

For this reason, with these platforms, a custom primer index 2 (SEQ ID NO:24 or SEQ ID NO:25 or SEQ ID NO:26) is used to allow the correct reading of index i5. Noteworthy is that the custom sequencing primer index 2 contains the LIB sequence. In detail, the custom primer index 2A (i5) [LNA-5'] (SEQ ID NO:24) and the custom primer index 2A (i5) [LNA-3'] (SEQ ID NO:25) have three LNA (Locked Nucleic Acid [LNA™]—Exiqon) modified nucleotides indicated in Table 1 with the "+" beside (e.g. "+A"). Furthermore, the custom primer index 2(i5) [RNA] (SEQ ID NO:26) is formed by fifteen RNA nucleotides indicated with the "r" beside (e.g. "rA").

The same considerations above apply mutatis mutandis when using the MALBAC compatible primers listed in Table 2 (SEQ ID NO:27 to SEQ ID NO:49).

As a further alternative embodiment, which allows the production of libraries suitable for all Illumina platforms (and in which the primary WGA library is a DRS-WGA library), the following combination of primers can be used:
at least one primer selected from the group consisting of SEQ ID NO:52 to SEQ ID NO:63;
at least one primer selected from the group consisting of SEQ ID NO:13 to SEQ ID NO:20;
primers SEQ ID NO:21 and SEQ ID NO:22;
a custom sequencing primer of SEQ ID NO:23 and a custom index 2 primer selected from the group consisting of SEQ ID NO:24, SEQ ID NO:25 and SEQ ID NO:26.

Primers from SEQ ID NO:52 to SEQ ID NO:63 include, instead of the RDSP sequence, a sequence of 8 nucleotides, which are needed 5' of the first primer 3' section to increase the annealing temperature of custom sequencing primers. It should be noted that the second primer (SEQ ID NO:13 to SEQ ID NO:20) includes the same sequence of 8 nucleotides 5' of the second primer 3' section. The custom sequencing primer of SEQ ID NO:23 is used for Illumina sequencing platforms to read the Read 1 and/or Read 2; the custom sequencing primer of SEQ ID NO:24 (or SEQ ID NO:25 or SEQ ID NO:26) is used for Illumina sequencing platforms to read the Index 1 and Index 2.

The following table summarizes the sequences of the DRS-WGA compatible primers for Illumina platforms according to this embodiment (sequences in 5'→3' direction, 5' and 3' omitted)

TABLE 3

| SEQID | Name | Primer sequence |
|---|---|---|
| SEQID52 | LIB_IL_v2_index D701 | CAAGCAGAAGACGGCATACGAGATCGAGTAATGCTCACCGAAGTGGGATTCCTGCTGTCAGTTAA |
| SEQID53 | LIB_IL_v2_index D702 | CAAGCAGAAGACGGCATACGAGATTCTCCGGAGCTCACCGAAGTGGGATTCCTGCTGTCAGTTAA |
| SEQID54 | LIB_IL_v2_index D703 | CAAGCAGAAGACGGCATACGAGATAATGAGCGGCTCACCGAAGTGGGATTCCTGCTGTCAGTTAA |
| SEQID55 | LIB_IL_v2_index D704 | CAAGCAGAAGACGGCATACGAGATGGAATCTCGCTCACCGAAGTGGGATTCCTGCTGTCAGTTAA |
| SEQID56 | LIB_IL_v2_index D705 | CAAGCAGAAGACGGCATACGAGATTTCTGAATGCTCACCGAAGTGGGATTCCTGCTGTCAGTTAA |
| SEQID57 | LIB_IL_v2_index D706 | CAAGCAGAAGACGGCATACGAGATACGAATTCGCTCACCGAAGTGGGATTCCTGCTGTCAGTTAA |
| SEQID58 | LIB_IL_v2_index D707 | CAAGCAGAAGACGGCATACGAGATAGCTTCAGGCTCACCGAAGTGGGATTCCTGCTGTCAGTTAA |
| SEQID59 | LIB_IL_v2_index D708 | CAAGCAGAAGACGGCATACGAGATGCGCATTAGCTCACCGAAGTGGGATTCCTGCTGTCAGTTAA |
| SEQID60 | LIB_IL_v2_index D709 | CAAGCAGAAGACGGCATACGAGATCATAGCCGGCTCACCGAAGTGGGATTCCTGCTGTCAGTTAA |
| SEQID61 | LIB_IL_v2_index D710 | CAAGCAGAAGACGGCATACGAGATTTCGCGGAGCTCACCGAAGTGGGATTCCTGCTGTCAGTTAA |
| SEQID62 | LIB_IL_v2_index D711 | CAAGCAGAAGACGGCATACGAGATGCGCGAGAGCTCACCGAAGTGGGATTCCTGCTGTCAGTTAA |
| SEQID63 | LIB_IL_v2_index D712 | CAAGCAGAAGACGGCATACGAGATCTATCGCTGCTCACCGAAGTGGGATTCCTGCTGTCAGTTAA |

As a further alternative embodiment, which allows the production of libraries suitable for all Illumina platforms (and in which the primary WGA library is a MALBAC library), the following combination of primers can be used:

at least one primer selected from the group consisting of SEQ ID NO:64 to SEQ ID NO:75;
at least one primer selected from the group consisting of SEQ ID NO:39 to SEQ ID NO:46;
primers SEQ ID NO:21 and SEQ ID NO:22;
a custom read primer of SEQ ID NO:47.

Preferably, also primer of SEQ ID NO:48 is used. Even more preferably, also primer of SEQ ID NO:49 is used.

The following table summarizes the sequences of the DRS-WGA compatible primers for Illumina platforms according to this embodiment (sequences in 5'→3' direction, 5' and 3' omitted)

TABLE 4

| SEQID | Name | sequence |
|---|---|---|
| SEQID64 | MAL_IL_v2_index D701 | CAAGCAGAAGACGGCATACGAGATCGAGTAATGTGAGTGATGGTTGAGGTAGTGTGGAG |
| SEQID65 | MAL_IL_v2_index D702 | CAAGCAGAAGACGGCATACGAGATTCTCCGGAGTGAGTGATGGTTGAGGTAGTGTGGAG |
| SEQID66 | MAL_IL_v2_index D703 | CAAGCAGAAGACGGCATACGAGATAATGAGCGGTGAGTGATGGTTGAGGTAGTGTGGAG |
| SEQID67 | MAL_IL_v2_index D704 | CAAGCAGAAGACGGCATACGAGATGGAATCTCGTGAGTGATGGTTGAGGTAGTGTGGAG |
| SEQID68 | MAL_IL_v2_index D705 | CAAGCAGAAGACGGCATACGAGATTTCTGAATGTGAGTGATGGTTGAGGTAGTGTGGAG |
| SEQID69 | MAL_IL_v2_index D706 | CAAGCAGAAGACGGCATACGAGATACGAATTCGTGAGTGATGGTTGAGGTAGTGTGGAG |
| SEQID70 | MAL_IL_v2_index D707 | CAAGCAGAAGACGGCATACGAGATAGCTTCAGGTGAGTGATGGTTGAGGTAGTGTGGAG |
| SEQID71 | MAL_IL_v2_index D708 | CAAGCAGAAGACGGCATACGAGATGCGCATTAGTGAGTGATGGTTGAGGTAGTGTGGAG |
| SEQID72 | MAL_IL_v2_index D709 | CAAGCAGAAGACGGCATACGAGATCATAGCCGGTGAGTGATGGTTGAGGTAGTGTGGAG |
| SEQID73 | MAL_IL_v2_index D710 | CAAGCAGAAGACGGCATACGAGATTTCGCGGAGTGAGTGATGGTTGAGGTAGTGTGGAG |
| SEQID74 | MAL_IL_v2_index D711 | CAAGCAGAAGACGGCATACGAGATGCGCGAGAGTGAGTGATGGTTGAGGTAGTGTGGAG |
| SEQID75 | MAL_IL_v2_index D712 | CAAGCAGAAGACGGCATACGAGATCTATCGCTGTGAGTGATGGTTGAGGTAGTGTGGAG |

Figure 4A:
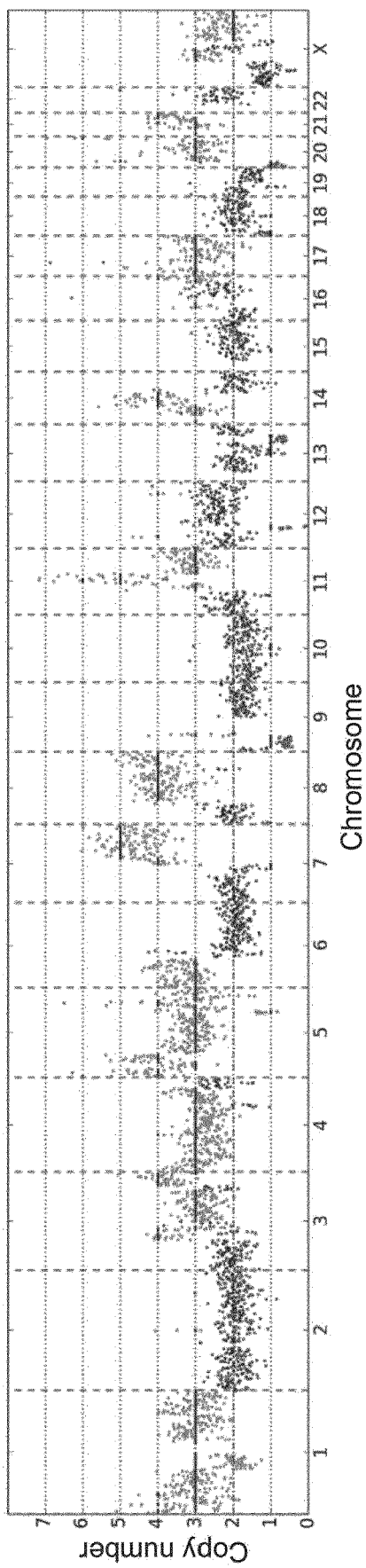
FIGS. 4A and 4B show sequencing results of a Low-pass Whole Genome Sequencing performed by the method according to the present invention. The figure shows copy number alterations (CNA) profiles of two single cells belonging to NCI-H441 and SW-480 cell lines, sorted by DEPArray™ (Menarini Silicon Biosystems) (FIG. 4A); and blood single cells (Circulating Tumor Cell [CTC] and White Blood Cell [WBC]), sorted by DEPArray™ (Menarini Silicon Biosystems) (FIG. 4B).
Figure 4A:
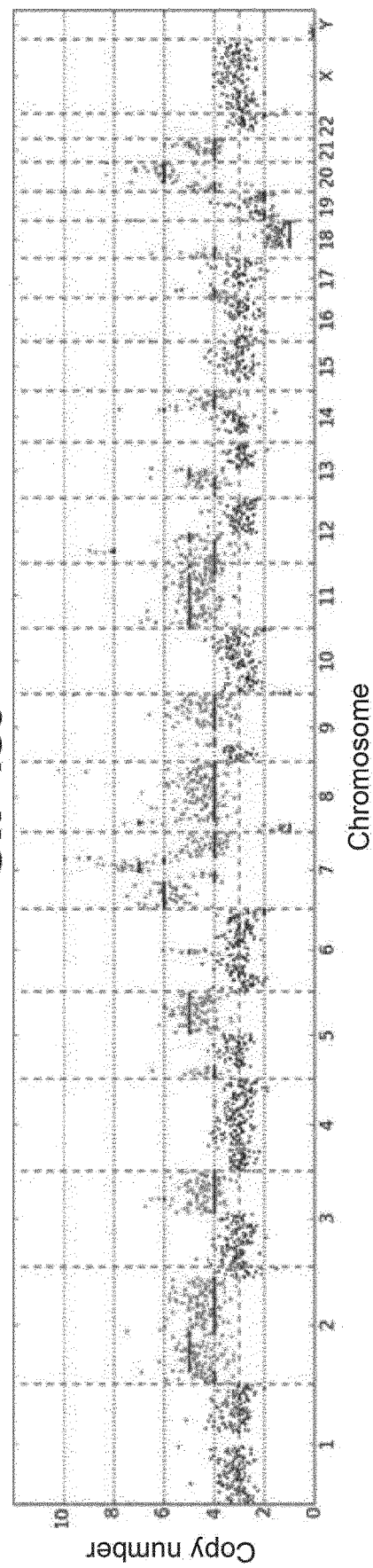
Figure 4B:
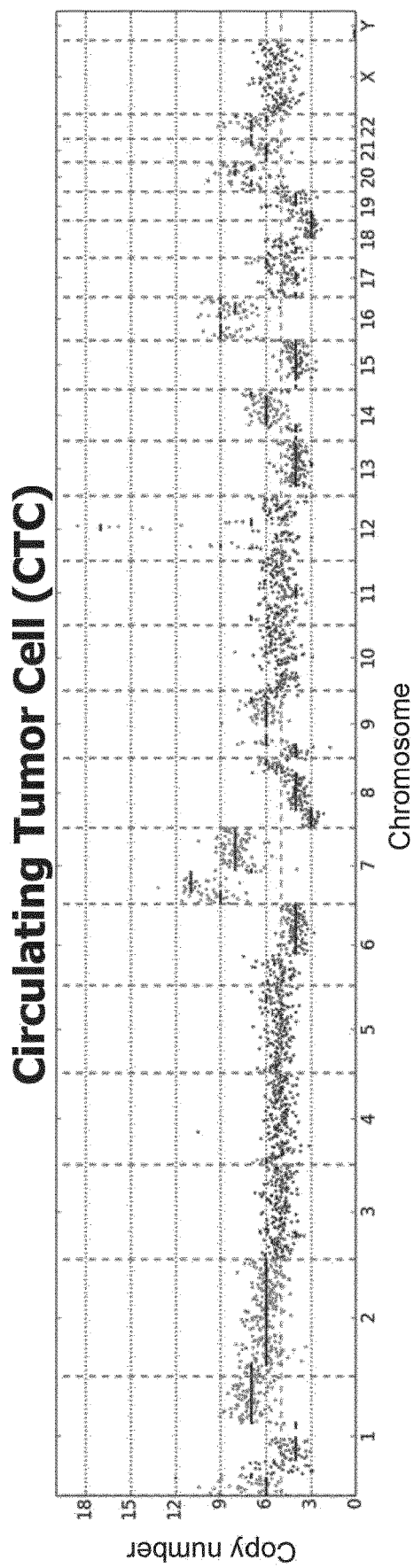
Figure 4B:
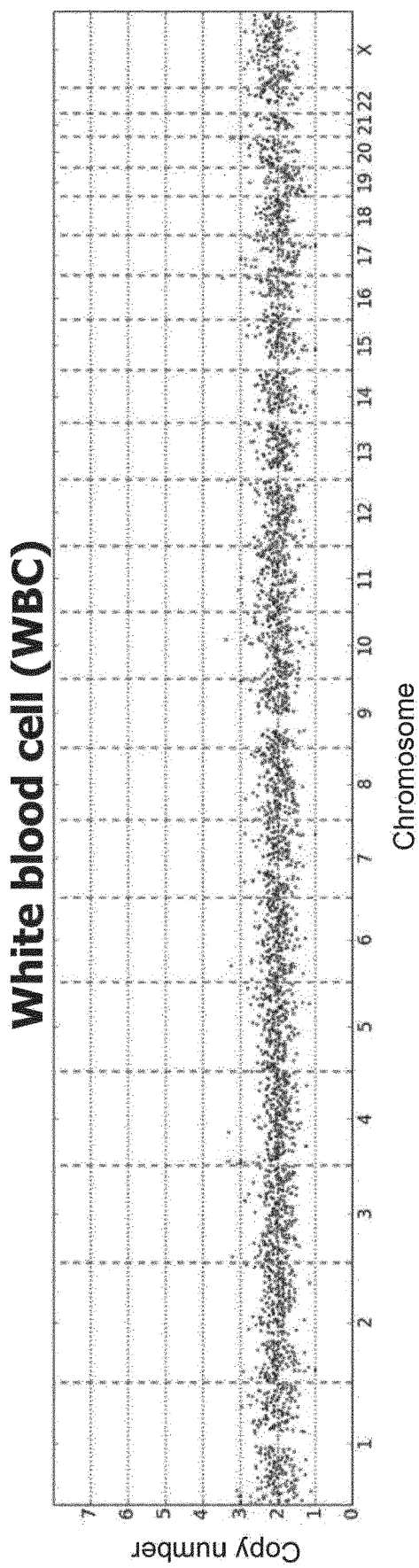

(Menarini Silicon Biosystems) and blood single cells, a circulating tumour cell (CTC) and a white blood cell (WBC) sorted by DEPArray™, were obtained using a custom python script, as shown in FIGS. 4A and 4B.

From the figures it can be noted that significant gains and losses are depicted, along the 22 autosomes, expressed as absolute copy numbers in sorted tumor single cells.

The ploidy values are indicated in the y-axis; providing a better fit of profiles with segmented data (black lines) and improving CNA calling. Dots above the main ploidy assessed can be considered gains; dots below the main ploidy assessed can be considered losses.

On the other hand, there is the absence of gains and losses in WBC normal cell as expected.

EXAMPLES

Example 1

Sequenced reads were aligned to the hg19 human reference genome using the BWA MEM algorithm (Li H. and Durbin R., 2010).

Control-FREEC (Boeva V. et al., 2011) algorithm was used to obtain copy-number calls without a control sample. Read counts were corrected by GC content and mappability (uniqMatch option) and window size were determined by software using coefficientOfVariation=0.06. Main ploidy parameter was set accordingly to ploidy of the genetic material tested and contamination adjustment was not used.

Plots for CNA profiles of two single cells belonging to NCI-441 and SW-480 cell lines, sorted by DEPArray™

Example 2

Figure 5:
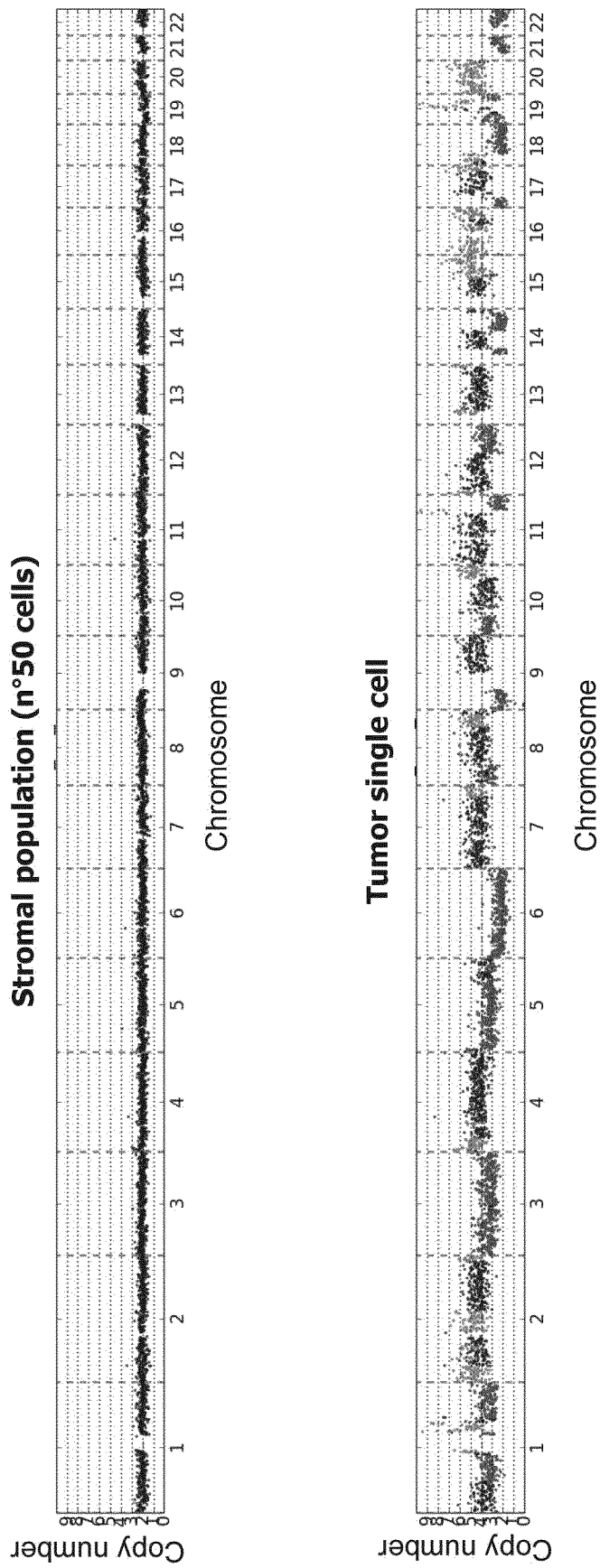
FIG. 5 shows sequencing results of a Low-pass Whole Genome Sequencing performed by the method according to the present invention. The figure shows copy number alterations (CNA) profiles of a tumor single cell and a population of 50 stromal cells, belonging to disaggregated FFPE section, digitally sorted by DEPArray™ (Menarini Silicon Biosystems) and whole-genome amplified using the Ampli1™ WGA kit.

A tumor single cell and a population of 50 stromal cells, belonging to a disaggregated FFPE section, were digitally sorted by DEPArray™ (Menarini Silicon Biosystems) and whole-genome amplified using the Ampli1™ WGA kit. FIG. 5 shows Low-pass Whole Genome Sequencing results performed by the method disclosed above. The figure shows copy number alterations (CNA) profiles, with gains and losses only for the tumor single cell. These high-quality CNA profiles demonstrate that the presented method is highly resilient to DNA degradation and proved to be a reliable and valuable method for the molecular characterization of tumour heterogeneity in FFPE tissues down to single level.

Example 3

Figure 6A:
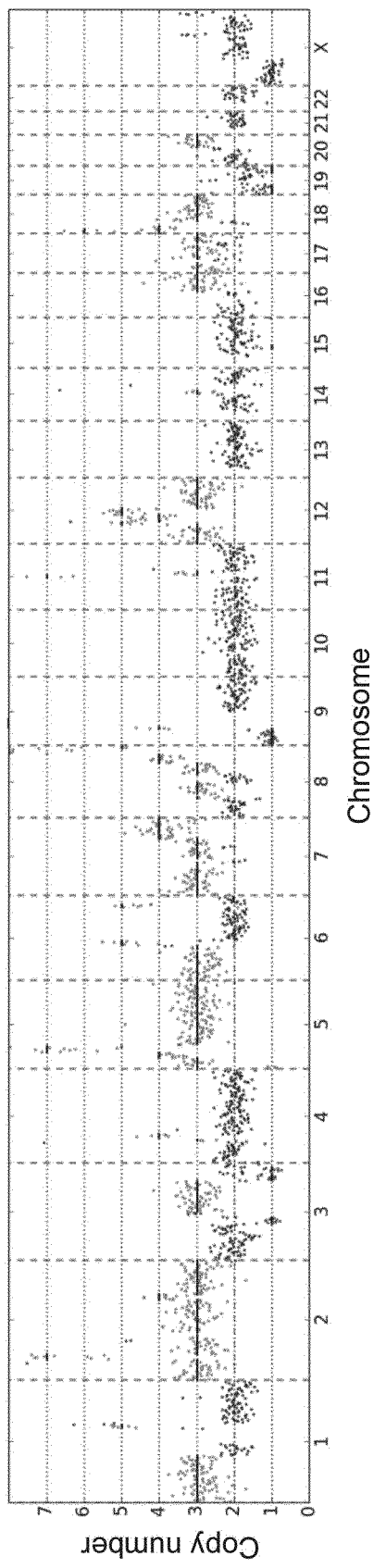
FIGS. 6A and 6B show inter-method and inter-platform (IonTorrent and Illumina) comparison results. In particular.
Figure 6A:
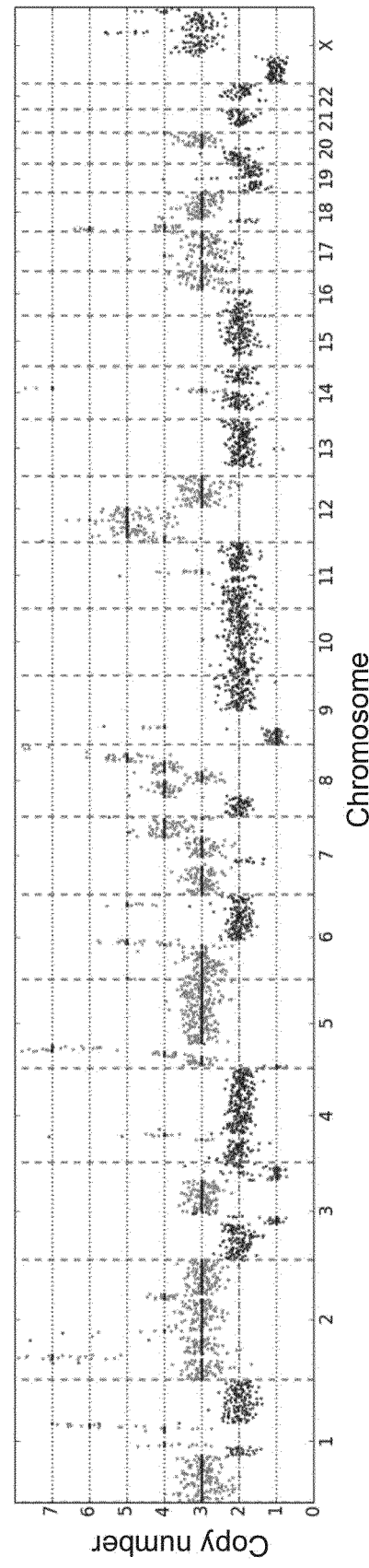
Figure 6B:
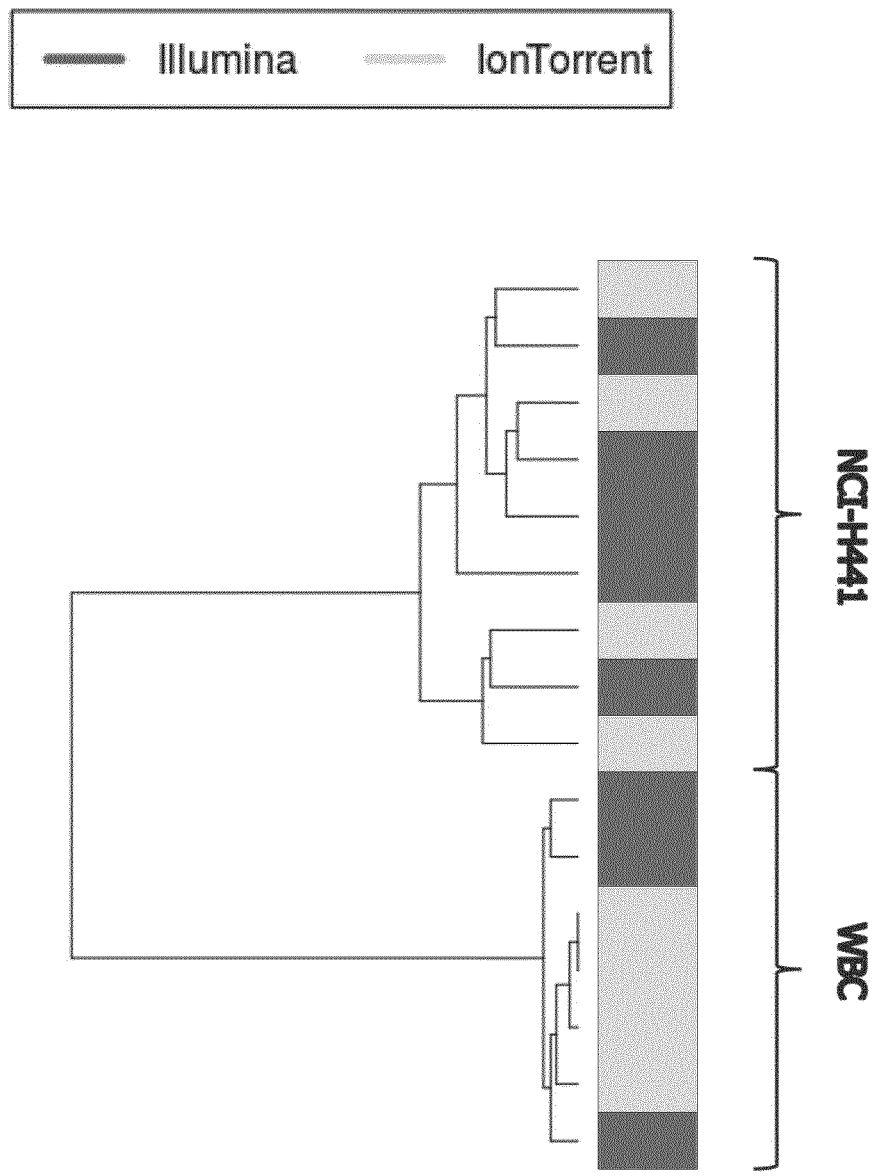

FIGS. 6A and 6B show inter-method and inter-platform (IonTorrent and Illumina) comparison results.

In particular, FIG. 6A shows copy number alterations (CNA) profiles of a NCI-H23 single cell, obtained with a Low-pass Whole Genome Sequencing method for IonTorrent (presented in PCT/EP2017/059075) and with the method according to the present invention for Illumina platforms. The results obtained with the two platforms are highly consistent with one another.

Furthermore, NCI-H441 and WBC single-cells hierarchical clustering, based on CNAs profiles, shows that samples are clustered by sample-types (tumor and normal) and not by methods or platforms (FIG. 6B).

In conclusion, both Ampli1™ LowPass methods for IonTorrent and for Illumina sequencing platforms show high concordance of CNA profiles.

Although the present invention has been described with reference to the method for Ampli1™ WGA only, the technique described, as will be apparent for the skilled in the art, clearly applies mutatis mutandis also to any other kind of WGA (e.g. MALBAC) which comprises a library with self-complementary 5' and 3' regions.

In an alternative embodiment of the present invention, the first or second primer (1PR and/or 2PR) could be modified so that they are bound at their 5' end to a solid support during at least one step of the procedure.

As an example the first primer (1PR) may comprise a Biotinylated 5' end. After the first PCR cycle (step b), streptavidin coated beads are added to the reaction tube, capturing the first-primer extended DNA library fragments, whereas non-extended fragments which do not comprise the first primer are eluted away, along with primers dNTPs and polymerase. In step c, the second primer (2PR) is provided (along with other PCR reagents) and hybridizes to the first-primer extended DNA library fragments and polymerization occurs using the bead-bound DNA library fragments left in the tube as template, producing a heteroadapter DNA fragment. After washing the reaction mix of step c, the heteroadapter can be further amplified by PCR (step d) in the same tube using third (3PR) and fourth (4PR) primers (along with other PCR reagents). Alternatively the heteroadapter can be denatured and eluted from the tube for further PCR amplification (step d) using third (3PR) and fourth (4PR) primers in a separate tube.

As another example, the first primer (1PR) may be bound covalently to magnetic beads. After the first PCR cycle (step b), the first-primer extended DNA library fragments are bound to the beads and retained, whereas non-extended fragments which comprise the known 3' sequence section (3SS) but do not comprise the first primer are eluted away. In step c, the second primer (2PR) hybridizes to the first-primer extended DNA library fragments known 3' sequence section (3SS) and polymerization occurs using the bead-bound DNA library fragments left in the tube as template, producing a heteroadapter DNA fragment. After washing the reaction mix of step c, the heteroadapter can be further amplified by PCR (step d) in the same tube using third (3PR) and fourth (4PR) primers. Alternatively the heteroadapter can be denatured and eluted from the tube for further PCR amplification (step d) using third (3PR) and fourth (4PR) primers in a separate tube.

One advantage of these embodiments, is that no size-selective effect linked to the use of SPRIbeads is introduced in the process. This will allow fragments of lengths smaller and/or larger than what normally retained by SPRIbeads, to be represented in the final sequenceable library. One disadvantage is the increased complexity of the kit reagents, inherent to conjugation of primers to beads or to Biotin. The presence of a broader range of fragments may be beneficial especially when pursuing whole genome sequencing at higher depth to achieve complete resquencing beyond the genome-wide copy number profiling by low-pass WGS.

As yet another example of embodiment, after the first primer (1PR) is used in the first PCR cycle (step b), a SPRI purification is carried out to remove residual first primer, then said second primer (2PR) conjugated to magnetic beads (either directly, through covalent bonds, or indirectly, through biotin modification of second primer and biotin-streptavidin interaction with streptavidin coated magnetic beads) is used in said single PCR cycle of step c, then the residual of reaction mix and mono-adapter fragments are eluted, magnetically retaining in the tube exclusively the resulting heteroadapter fragments, before proceeding to—step d—the PCR amplification with said third (3PR) and fourth (4PR) primer.

Advantages

The method of generating a massively parallel sequencing library according to the present invention allows to obtain a library including only heteroadapter fragments for those sequencing platforms which require so, in a rapid, efficient, reliable and cost-effective manner. Not least, it allows to generate double strand DNA and sequencing-ready libraries with a streamlined, single-day and single-tube workflow.

Finally, the advantages of low pass whole genome sequencing with respect to array CGH (aCGH)—the current leading technology for investigating CNV—should be highlighted. Array CGH (aCGH) is based on the use of differentially labeled test and reference genomic DNA samples that are simultaneously hybridized to DNA targets arrayed on a glass slide or other solid platform. However, limitations remain for certain applications as it has proved difficult to use low quality/quantity of DNA. Moreover, chromosomal copy number assessment based on a low-pass whole genome sequencing method may offer several advantages compared to aCGH including reduced DNA sequencing cost, enhanced detection of partial or segmental aneuploidies as a result of the potential increase in chromosomal analysis resolution, control-free calling of copy number alterations. In addition, the potential automation of the sequencing library preparation allows to minimize human errors, reduce hands-on time, and enable higher throughput and consistency.

The invention claimed is:

1. A method of generating a massively parallel sequencing library comprising the steps of:
   (a) providing a primary whole genome amplification (WGA) DNA library (pWGAlib) including fragments comprising a known 5' sequence section (5SS), a middle sequence section (MSS), and a known 3' sequence section (3SS) reverse complementary to the known 5' sequence section, the known 5' sequence section (5SS) comprising a WGA library universal sequence adapter, and the middle sequence section (MSS) comprising at least an insert section (IS), corresponding to a DNA sequence of the original unamplified DNA prior to WGA;
   (b) performing a PCR cycle consisting of a single round of PCR on the primary WGA DNA library using at least one first primer (1PR) comprising at least a first primer 5' section (1PR5S) and a first primer 3' section (1PR3S), the first primer 5' section (1PR5S) comprising at least one first sequencing adapter (1PR5SA), and the first primer 3' section (1PR3S) hybridizing to the known 3' sequence section (3SS), so as to obtain a first primer extended WGA DNA library;
   (c) performing a PCR cycle consisting of a single round of PCR on the first primer extended WGA DNA library produced by step (b) using at least one second primer (2PR) comprising a second primer 5' section (2PR5S) and a second primer 3' section (2PR3S), the second primer 5' section (2PR5S) comprising at least one second sequencing adapter (2PR5SA) different from the at least one first sequencing adapter (1PR5SA), and the second primer 3' section (2PR3S) hybridizing to the known 3' sequence section (3SS), so as to obtain a first primer extended WGA DNA library and a second primer extended WGA DNA library; and, (d) amplifying by PCR the first primer extended WGA DNA library and the second primer extended WGA DNA library using at least one third primer (3PR) comprising the first sequencing adapter (1PR5SA) and at least one fourth primer (4PR) comprising the second sequencing adapter (2PR5SA), so as to obtain an amplified first and second primer extended WGA DNA libraries.

2. The method according to claim 1, wherein the at least one first primer (1PR) further comprises at least one read sequencing primer sequence (1PRSEQ) in 3' position of the first primer 5' section (1PR5S) and in 5' position of the first primer 3' section (1PR3S).

3. The method according to claim 1, wherein the first primer 5' section (1PR5S) further comprises at least one first sequencing barcode (1PR5BC), in 3' position of the at least one first sequencing adapter (1PR5SA) and in 5' position of the first primer 3' section (1PR3S) and/or the second primer 5' section (2PR5S) further comprises at least one second sequencing barcode (2PR5BC), in 3' position of the at least one second sequencing adapter (2PR5SA) and in 5' position of the second primer 3' section (2PR3S).

4. The method according to claim 1, further comprising a step of purifying the first primer extended WGA DNA library after step b and/or further comprising a step of purifying the first and second primer extended WGA DNA libraries after step c and/or further comprising a step of purifying the amplified first and second primer extended WGA DNA library after step d.

5. The method according to claim 1, wherein the WGA library universal sequence adapter is a DRS-WGA library universal sequence adapter or a MALBAC library universal sequence adapter.

6. The method according to claim 5, wherein the WGA library universal sequence adapter is a DRS-WGA library universal sequence adapter.

7. The method according to claim 5, wherein the DRS-WGA library universal sequence adapter is SEQ ID NO:50 and the MALBAC library universal sequence adapter is SEQ ID NO:51.

8. The method of claim 1, wherein the middle sequence section (MSS) further comprises a flanking 5' intermediate section (F5) and/or a flanking 3' intermediate section (F3).

* * * * *

SEQUENCE LISTING

<160> NUMBER OF SEQ ID NOS: 75

<210> SEQ ID NO 1
<211> LENGTH: 87
<212> TYPE: DNA

<213> ORGANISM: Artificial Sequence
<220> FEATURE:
<223> OTHER INFORMATION: LIB_IL_index D701

<400> SEQUENCE: 1

```
caagcagaag acggcatacg agatcgagta atgtgactgg agttcagacg tgtgctcttc    60
cgatctagtg ggattcctgc tgtcagt                                        87
```

<210> SEQ ID NO 2
<211> LENGTH: 87
<212> TYPE: DNA
<213> ORGANISM: Artificial Sequence
<220> FEATURE:
<223> OTHER INFORMATION: LIB_IL_index D702

<400> SEQUENCE: 2

```
caagcagaag acggcatacg agattctccg gagtgactgg agttcagacg tgtgctcttc    60
cgatctagtg ggattcctgc tgtcagt                                        87
```

<210> SEQ ID NO 3
<211> LENGTH: 87
<212> TYPE: DNA
<213> ORGANISM: Artificial Sequence
<220> FEATURE:
<223> OTHER INFORMATION: LIB_IL_index D703

<400> SEQUENCE: 3

```
caagcagaag acggcatacg agataatgag cggtgactgg agttcagacg tgtgctcttc    60
cgatctagtg ggattcctgc tgtcagt                                        87
```

<210> SEQ ID NO 4
<211> LENGTH: 87
<212> TYPE: DNA
<213> ORGANISM: Artificial Sequence
<220> FEATURE:
<223> OTHER INFORMATION: LIB_IL_index D704

<400> SEQUENCE: 4

```
caagcagaag acggcatacg agatggaatc tcgtgactgg agttcagacg tgtgctcttc    60
cgatctagtg ggattcctgc tgtcagt                                        87
```

<210> SEQ ID NO 5
<211> LENGTH: 87
<212> TYPE: DNA
<213> ORGANISM: Artificial Sequence
<220> FEATURE:
<223> OTHER INFORMATION: LIB_IL_index D705

<400> SEQUENCE: 5

```
caagcagaag acggcatacg agatttctga atgtgactgg agttcagacg tgtgctcttc    60
cgatctagtg ggattcctgc tgtcagt                                        87
```

<210> SEQ ID NO 6
<211> LENGTH: 87
<212> TYPE: DNA
<213> ORGANISM: Artificial Sequence
<220> FEATURE:
<223> OTHER INFORMATION: LIB_IL_index D706

<400> SEQUENCE: 6

```
caagcagaag acggcatacg agatacgaat tcgtgactgg agttcagacg tgtgctcttc    60
cgatctagtg ggattcctgc tgtcagt                                        87
```

<210> SEQ ID NO 7
<211> LENGTH: 87
<212> TYPE: DNA
<213> ORGANISM: Artificial Sequence
<220> FEATURE:
<223> OTHER INFORMATION: LIB_IL_index D707

<400> SEQUENCE: 7
caagcagaag acggcatacg agatagcttc aggtgactgg agttcagacg tgtgctcttc    60
cgatctagtg ggattcctgc tgtcagt                                         87

<210> SEQ ID NO 8
<211> LENGTH: 87
<212> TYPE: DNA
<213> ORGANISM: Artificial Sequence
<220> FEATURE:
<223> OTHER INFORMATION: LIB_IL_index D708

<400> SEQUENCE: 8
caagcagaag acggcatacg agatgcgcat tagtgactgg agttcagacg tgtgctcttc    60
cgatctagtg ggattcctgc tgtcagt                                         87

<210> SEQ ID NO 9
<211> LENGTH: 87
<212> TYPE: DNA
<213> ORGANISM: Artificial Sequence
<220> FEATURE:
<223> OTHER INFORMATION: LIB_IL_index D709

<400> SEQUENCE: 9
caagcagaag acggcatacg agatcatagc cggtgactgg agttcagacg tgtgctcttc    60
cgatctagtg ggattcctgc tgtcagt                                         87

<210> SEQ ID NO 10
<211> LENGTH: 87
<212> TYPE: DNA
<213> ORGANISM: Artificial Sequence
<220> FEATURE:
<223> OTHER INFORMATION: LIB_IL_index D710

<400> SEQUENCE: 10
caagcagaag acggcatacg agatttcgcg gagtgactgg agttcagacg tgtgctcttc    60
cgatctagtg ggattcctgc tgtcagt                                         87

<210> SEQ ID NO 11
<211> LENGTH: 87
<212> TYPE: DNA
<213> ORGANISM: Artificial Sequence
<220> FEATURE:
<223> OTHER INFORMATION: LIB_IL_index D711

<400> SEQUENCE: 11
caagcagaag acggcatacg agatgcgcga gagtgactgg agttcagacg tgtgctcttc    60
cgatctagtg ggattcctgc tgtcagt                                         87

<210> SEQ ID NO 12
<211> LENGTH: 87
<212> TYPE: DNA
<213> ORGANISM: Artificial Sequence
<220> FEATURE:
<223> OTHER INFORMATION: LIB_IL_index D712

```
<400> SEQUENCE: 12
caagcagaag acggcatacg agatctatcg ctgtgactgg agttcagacg tgtgctcttc      60
cgatctagtg ggattcctgc tgtcagt                                          87

<210> SEQ ID NO 13
<211> LENGTH: 70
<212> TYPE: DNA
<213> ORGANISM: Artificial Sequence
<220> FEATURE:
<223> OTHER INFORMATION: LIB_IL_index D501

<400> SEQUENCE: 13
aatgatacgg cgaccaccga gatctacact atagcctgct caccgaagtg ggattcctgc      60
tgtcagttaa                                                             70

<210> SEQ ID NO 14
<211> LENGTH: 70
<212> TYPE: DNA
<213> ORGANISM: Artificial Sequence
<220> FEATURE:
<223> OTHER INFORMATION: LIB_IL_index D502

<400> SEQUENCE: 14
aatgatacgg cgaccaccga gatctacaca tagaggcgct caccgaagtg ggattcctgc      60
tgtcagttaa                                                             70

<210> SEQ ID NO 15
<211> LENGTH: 70
<212> TYPE: DNA
<213> ORGANISM: Artificial Sequence
<220> FEATURE:
<223> OTHER INFORMATION: LIB_IL_index D503

<400> SEQUENCE: 15
aatgatacgg cgaccaccga gatctacacc ctatcctgct caccgaagtg ggattcctgc      60
tgtcagttaa                                                             70

<210> SEQ ID NO 16
<211> LENGTH: 70
<212> TYPE: DNA
<213> ORGANISM: Artificial Sequence
<220> FEATURE:
<223> OTHER INFORMATION: LIB_IL_index D504

<400> SEQUENCE: 16
aatgatacgg cgaccaccga gatctacacg gctctgagct caccgaagtg ggattcctgc      60
tgtcagttaa                                                             70

<210> SEQ ID NO 17
<211> LENGTH: 70
<212> TYPE: DNA
<213> ORGANISM: Artificial Sequence
<220> FEATURE:
<223> OTHER INFORMATION: LIB_IL_index D505

<400> SEQUENCE: 17
aatgatacgg cgaccaccga gatctacaca ggcgaaggct caccgaagtg ggattcctgc      60
tgtcagttaa                                                             70

<210> SEQ ID NO 18
<211> LENGTH: 70
```

```
<212> TYPE: DNA
<213> ORGANISM: Artificial Sequence
<220> FEATURE:
<223> OTHER INFORMATION: LIB_IL_index D506

<400> SEQUENCE: 18
aatgatacgg cgaccaccga gatctacact aatcttagct caccgaagtg ggattcctgc    60
tgtcagttaa                                                          70

<210> SEQ ID NO 19
<211> LENGTH: 70
<212> TYPE: DNA
<213> ORGANISM: Artificial Sequence
<220> FEATURE:
<223> OTHER INFORMATION: LIB_IL_index D507

<400> SEQUENCE: 19
aatgatacgg cgaccaccga gatctacacc aggacgtgct caccgaagtg ggattcctgc    60
tgtcagttaa                                                          70

<210> SEQ ID NO 20
<211> LENGTH: 70
<212> TYPE: DNA
<213> ORGANISM: Artificial Sequence
<220> FEATURE:
<223> OTHER INFORMATION: LIB_IL_index D508

<400> SEQUENCE: 20
aatgatacgg cgaccaccga gatctacacg tactgacgct caccgaagtg ggattcctgc    60
tgtcagttaa                                                          70

<210> SEQ ID NO 21
<211> LENGTH: 23
<212> TYPE: DNA
<213> ORGANISM: Artificial Sequence
<220> FEATURE:
<223> OTHER INFORMATION: Adapter P5

<400> SEQUENCE: 21
aatgatacgg cgaccaccga gat                                           23

<210> SEQ ID NO 22
<211> LENGTH: 21
<212> TYPE: DNA
<213> ORGANISM: Artificial Sequence
<220> FEATURE:
<223> OTHER INFORMATION: Adapter P7

<400> SEQUENCE: 22
caagcagaag acggcatacg a                                             21

<210> SEQ ID NO 23
<211> LENGTH: 33
<212> TYPE: DNA
<213> ORGANISM: Artificial Sequence
<220> FEATURE:
<223> OTHER INFORMATION: Ampli1 custom sequencing primer

<400> SEQUENCE: 23
gctcaccgaa gtgggattcc tgctgtcagt taa                                33

<210> SEQ ID NO 24
<211> LENGTH: 26
<212> TYPE: DNA
```

<213> ORGANISM: Artificial Sequence
<220> FEATURE:
<223> OTHER INFORMATION: Custom primer index 2 A (i5) [LNA-5]
<220> FEATURE:
<221> NAME/KEY: misc_feature
<222> LOCATION: (2)..(2)
<223> OTHER INFORMATION: /note="locked nucleic acid"
<220> FEATURE:
<221> NAME/KEY: misc_feature
<222> LOCATION: (6)..(6)
<223> OTHER INFORMATION: /note="locked nucleic acid"
<220> FEATURE:
<221> NAME/KEY: misc_feature
<222> LOCATION: (11)..(11)
<223> OTHER INFORMATION: /note="locked nucleic acid"

<400> SEQUENCE: 24
acagcaggaa tcccacttcg gtgagc                                         26

<210> SEQ ID NO 25
<211> LENGTH: 26
<212> TYPE: DNA
<213> ORGANISM: Artificial Sequence
<220> FEATURE:
<223> OTHER INFORMATION: Custom primer index 2 A (i5) [LNA-3]
<220> FEATURE:
<221> NAME/KEY: misc_feature
<222> LOCATION: (18)..(18)
<223> OTHER INFORMATION: /note="locked nucleic acid"
<220> FEATURE:
<221> NAME/KEY: misc_feature
<222> LOCATION: (22)..(22)
<223> OTHER INFORMATION: /note="locked nucleic acid"
<220> FEATURE:
<221> NAME/KEY: misc_feature
<222> LOCATION: (24)..(24)
<223> OTHER INFORMATION: /note="locked nucleic acid"

<400> SEQUENCE: 25
acagcaggaa tcccacttcg gtgagc                                         26

<210> SEQ ID NO 26
<211> LENGTH: 33
<212> TYPE: DNA
<213> ORGANISM: Artificial Sequence
<220> FEATURE:
<223> OTHER INFORMATION: Custom primer index 2(i5)[RNA]
<220> FEATURE:
<221> NAME/KEY: misc_feature
<222> LOCATION: (3)..(3)
<223> OTHER INFORMATION: /note="5-carbon sugar is ribose"
<220> FEATURE:
<221> NAME/KEY: misc_feature
<222> LOCATION: (5)..(5)
<223> OTHER INFORMATION: /note="5-carbon sugar is ribose"
<220> FEATURE:
<221> NAME/KEY: misc_feature
<222> LOCATION: (7)..(7)
<223> OTHER INFORMATION: /note="5-carbon sugar is ribose"
<220> FEATURE:
<221> NAME/KEY: misc_feature
<222> LOCATION: (8)..(8)
<223> OTHER INFORMATION: /note="5-carbon sugar is ribose"
<220> FEATURE:
<221> NAME/KEY: misc_feature
<222> LOCATION: (11)..(11)
<223> OTHER INFORMATION: /note="5-carbon sugar is ribose"
<220> FEATURE:
<221> NAME/KEY: misc_feature
<222> LOCATION: (12)..(12)
<223> OTHER INFORMATION: /note="5-carbon sugar is ribose"
<220> FEATURE:
<221> NAME/KEY: misc_feature
<222> LOCATION: (15)..(15)
<223> OTHER INFORMATION: /note="5-carbon sugar is ribose"

```
<220> FEATURE:
<221> NAME/KEY: misc_feature
<222> LOCATION: (17)..(17)
<223> OTHER INFORMATION: /note="5-carbon sugar is ribose"
<220> FEATURE:
<221> NAME/KEY: misc_feature
<222> LOCATION: (21)..(21)
<223> OTHER INFORMATION: /note="5-carbon sugar is ribose"
<220> FEATURE:
<221> NAME/KEY: misc_feature
<222> LOCATION: (22)..(22)
<223> OTHER INFORMATION: /note="5-carbon sugar is ribose"
<220> FEATURE:
<221> NAME/KEY: misc_feature
<222> LOCATION: (23)..(23)
<223> OTHER INFORMATION: /note="5-carbon sugar is ribose"
<220> FEATURE:
<221> NAME/KEY: misc_feature
<222> LOCATION: (26)..(26)
<223> OTHER INFORMATION: /note="5-carbon sugar is ribose"
<220> FEATURE:
<221> NAME/KEY: misc_feature
<222> LOCATION: (29)..(29)
<223> OTHER INFORMATION: /note="5-carbon sugar is ribose"
<220> FEATURE:
<221> NAME/KEY: misc_feature
<222> LOCATION: (30)..(30)
<223> OTHER INFORMATION: /note="5-carbon sugar is ribose"
<220> FEATURE:
<221> NAME/KEY: misc_feature
<222> LOCATION: (31)..(31)
<223> OTHER INFORMATION: /note="5-carbon sugar is ribose"

<400> SEQUENCE: 26
ttaactgaca gcaggaatcc cactacggag agc                            33

<210> SEQ ID NO 27
<211> LENGTH: 93
<212> TYPE: DNA
<213> ORGANISM: Artificial Sequence
<220> FEATURE:
<223> OTHER INFORMATION: MAL_IL_index D701

<400> SEQUENCE: 27
caagcagaag acggcatacg agatcgagta atgtgactgg agttcagacg tgtgctcttc    60
cgatctgtga gtgatggttg aggtagtgtg gag                                 93

<210> SEQ ID NO 28
<211> LENGTH: 93
<212> TYPE: DNA
<213> ORGANISM: Artificial Sequence
<220> FEATURE:
<223> OTHER INFORMATION: MAL_IL_index D702

<400> SEQUENCE: 28
caagcagaag acggcatacg agattctccg gagtgactgg agttcagacg tgtgctcttc    60
cgatctgtga gtgatggttg aggtagtgtg gag                                 93

<210> SEQ ID NO 29
<211> LENGTH: 93
<212> TYPE: DNA
<213> ORGANISM: Artificial Sequence
<220> FEATURE:
<223> OTHER INFORMATION: MAL_IL_index D703

<400> SEQUENCE: 29
caagcagaag acggcatacg agataatgag cggtgactgg agttcagacg tgtgctcttc    60
cgatctgtga gtgatggttg aggtagtgtg gag                                 93
```

<210> SEQ ID NO 30
<211> LENGTH: 93
<212> TYPE: DNA
<213> ORGANISM: Artificial Sequence
<220> FEATURE:
<223> OTHER INFORMATION: MAL_IL_index D704

<400> SEQUENCE: 30
caagcagaag acggcatacg agatggaatc tcgtgactgg agttcagacg tgtgctcttc    60
cgatctgtga gtgatggttg aggtagtgtg gag                                 93

<210> SEQ ID NO 31
<211> LENGTH: 93
<212> TYPE: DNA
<213> ORGANISM: Artificial Sequence
<220> FEATURE:
<223> OTHER INFORMATION: MAL_IL_index D705

<400> SEQUENCE: 31
caagcagaag acggcatacg agatttctga atgtgactgg agttcagacg tgtgctcttc    60
cgatctgtga gtgatggttg aggtagtgtg gag                                 93

<210> SEQ ID NO 32
<211> LENGTH: 93
<212> TYPE: DNA
<213> ORGANISM: Artificial Sequence
<220> FEATURE:
<223> OTHER INFORMATION: MAL_IL_index D706

<400> SEQUENCE: 32
caagcagaag acggcatacg agatacgaat tcgtgactgg agttcagacg tgtgctcttc    60
cgatctgtga gtgatggttg aggtagtgtg gag                                 93

<210> SEQ ID NO 33
<211> LENGTH: 93
<212> TYPE: DNA
<213> ORGANISM: Artificial Sequence
<220> FEATURE:
<223> OTHER INFORMATION: MAL_IL_index D707

<400> SEQUENCE: 33
caagcagaag acggcatacg agatagcttc aggtgactgg agttcagacg tgtgctcttc    60
cgatctgtga gtgatggttg aggtagtgtg gag                                 93

<210> SEQ ID NO 34
<211> LENGTH: 93
<212> TYPE: DNA
<213> ORGANISM: Artificial Sequence
<220> FEATURE:
<223> OTHER INFORMATION: MAL_IL_index D708

<400> SEQUENCE: 34
caagcagaag acggcatacg agatgcgcat tagtgactgg agttcagacg tgtgctcttc    60
cgatctgtga gtgatggttg aggtagtgtg gag                                 93

<210> SEQ ID NO 35
<211> LENGTH: 93
<212> TYPE: DNA
<213> ORGANISM: Artificial Sequence
<220> FEATURE:
<223> OTHER INFORMATION: MAL_IL_index D709

<400> SEQUENCE: 35

```
caagcagaag acggcatacg agatcatagc cggtgactgg agttcagacg tgtgctcttc    60
cgatctgtga gtgatggttg aggtagtgtg gag                                93
```

<210> SEQ ID NO 36
<211> LENGTH: 93
<212> TYPE: DNA
<213> ORGANISM: Artificial Sequence
<220> FEATURE:
<223> OTHER INFORMATION: MAL_IL_index D710

<400> SEQUENCE: 36

```
caagcagaag acggcatacg agatttcgcg gagtgactgg agttcagacg tgtgctcttc    60
cgatctgtga gtgatggttg aggtagtgtg gag                                93
```

<210> SEQ ID NO 37
<211> LENGTH: 93
<212> TYPE: DNA
<213> ORGANISM: Artificial Sequence
<220> FEATURE:
<223> OTHER INFORMATION: MAL_IL_index D711

<400> SEQUENCE: 37

```
caagcagaag acggcatacg agatgcgcga gagtgactgg agttcagacg tgtgctcttc    60
cgatctgtga gtgatggttg aggtagtgtg gag                                93
```

<210> SEQ ID NO 38
<211> LENGTH: 93
<212> TYPE: DNA
<213> ORGANISM: Artificial Sequence
<220> FEATURE:
<223> OTHER INFORMATION: MAL_IL_index D712

<400> SEQUENCE: 38

```
caagcagaag acggcatacg agatctatcg ctgtgactgg agttcagacg tgtgctcttc    60
cgatctgtga gtgatggttg aggtagtgtg gag                                93
```

<210> SEQ ID NO 39
<211> LENGTH: 64
<212> TYPE: DNA
<213> ORGANISM: Artificial Sequence
<220> FEATURE:
<223> OTHER INFORMATION: MAL_IL_index D501

<400> SEQUENCE: 39

```
aatgatacgg cgaccaccga gatctacact atagcctgtg agtgatggtt gaggtagtgt    60
ggag                                                                64
```

<210> SEQ ID NO 40
<211> LENGTH: 64
<212> TYPE: DNA
<213> ORGANISM: Artificial Sequence
<220> FEATURE:
<223> OTHER INFORMATION: MAL_IL_index D502

<400> SEQUENCE: 40

```
aatgatacgg cgaccaccga gatctacaca tagaggcgtg agtgatggtt gaggtagtgt    60
ggag                                                                64
```

<210> SEQ ID NO 41
<211> LENGTH: 64
<212> TYPE: DNA

```
<213> ORGANISM: Artificial Sequence
<220> FEATURE:
<223> OTHER INFORMATION: MAL_IL_index D503

<400> SEQUENCE: 41
aatgatacgg cgaccaccga gatctacacc ctatcctgtg agtgatggtt gaggtagtgt    60
ggag                                                                 64

<210> SEQ ID NO 42
<211> LENGTH: 64
<212> TYPE: DNA
<213> ORGANISM: Artificial Sequence
<220> FEATURE:
<223> OTHER INFORMATION: MAL_IL_index D504

<400> SEQUENCE: 42
aatgatacgg cgaccaccga gatctacacg gctctgagtg agtgatggtt gaggtagtgt    60
ggag                                                                 64

<210> SEQ ID NO 43
<211> LENGTH: 64
<212> TYPE: DNA
<213> ORGANISM: Artificial Sequence
<220> FEATURE:
<223> OTHER INFORMATION: MAL_IL_index D505

<400> SEQUENCE: 43
aatgatacgg cgaccaccga gatctacaca ggcgaaggtg agtgatggtt gaggtagtgt    60
ggag                                                                 64

<210> SEQ ID NO 44
<211> LENGTH: 64
<212> TYPE: DNA
<213> ORGANISM: Artificial Sequence
<220> FEATURE:
<223> OTHER INFORMATION: MAL_IL_index D506

<400> SEQUENCE: 44
aatgatacgg cgaccaccga gatctacact aatcttagtg agtgatggtt gaggtagtgt    60
ggag                                                                 64

<210> SEQ ID NO 45
<211> LENGTH: 64
<212> TYPE: DNA
<213> ORGANISM: Artificial Sequence
<220> FEATURE:
<223> OTHER INFORMATION: MAL_IL_index D507

<400> SEQUENCE: 45
aatgatacgg cgaccaccga gatctacacc aggacgtgtg agtgatggtt gaggtagtgt    60
ggag                                                                 64

<210> SEQ ID NO 46
<211> LENGTH: 64
<212> TYPE: DNA
<213> ORGANISM: Artificial Sequence
<220> FEATURE:
<223> OTHER INFORMATION: MAL_IL_index D508

<400> SEQUENCE: 46
aatgatacgg cgaccaccga gatctacacg tactgacgtg agtgatggtt gaggtagtgt    60
ggag                                                                 64
```

<210> SEQ ID NO 47
<211> LENGTH: 27
<212> TYPE: DNA
<213> ORGANISM: Artificial Sequence
<220> FEATURE:
<223> OTHER INFORMATION: Custom Read 1 primer

<400> SEQUENCE: 47
gtgagtgatg gttgaggtag tgtggag                                27

<210> SEQ ID NO 48
<211> LENGTH: 27
<212> TYPE: DNA
<213> ORGANISM: Artificial Sequence
<220> FEATURE:
<223> OTHER INFORMATION: Custom primer index 1 (i7)

<400> SEQUENCE: 48
ctccacacta cctcaaccat cactcac                                27

<210> SEQ ID NO 49
<211> LENGTH: 33
<212> TYPE: DNA
<213> ORGANISM: Artificial Sequence
<220> FEATURE:
<223> OTHER INFORMATION: Custom primer read 2 (optional)

<400> SEQUENCE: 49
gctcaccgaa gtgggattcc tgctgtcagt taa                         33

<210> SEQ ID NO 50
<211> LENGTH: 21
<212> TYPE: DNA
<213> ORGANISM: Artificial Sequence
<220> FEATURE:
<223> OTHER INFORMATION: LIB

<400> SEQUENCE: 50
agtgggattc ctgctgtcag t                                      21

<210> SEQ ID NO 51
<211> LENGTH: 27
<212> TYPE: DNA
<213> ORGANISM: Artificial Sequence
<220> FEATURE:
<223> OTHER INFORMATION: MALBAC

<400> SEQUENCE: 51
gtgagtgatg gttgaggtag tgtggag                                27

<210> SEQ ID NO 52
<211> LENGTH: 65
<212> TYPE: DNA
<213> ORGANISM: Artificial Sequence
<220> FEATURE:
<223> OTHER INFORMATION: LIB_IL_v2_index D701

<400> SEQUENCE: 52
caagcagaag acggcatacg agatcgagta atgctcaccg aagtgggatt cctgctgtca    60
gttaa                                                        65

<210> SEQ ID NO 53
<211> LENGTH: 65
<212> TYPE: DNA

```
<213> ORGANISM: Artificial Sequence
<220> FEATURE:
<223> OTHER INFORMATION: LIB_IL_v2_index D702

<400> SEQUENCE: 53
caagcagaag acggcatacg agattctccg gagctcaccg aagtgggatt cctgctgtca    60
gttaa                                                                65

<210> SEQ ID NO 54
<211> LENGTH: 65
<212> TYPE: DNA
<213> ORGANISM: Artificial Sequence
<220> FEATURE:
<223> OTHER INFORMATION: LIB_IL_v2_index D703

<400> SEQUENCE: 54
caagcagaag acggcatacg agataatgag cggctcaccg aagtgggatt cctgctgtca    60
gttaa                                                                65

<210> SEQ ID NO 55
<211> LENGTH: 65
<212> TYPE: DNA
<213> ORGANISM: Artificial Sequence
<220> FEATURE:
<223> OTHER INFORMATION: LIB_IL_v2_index D704

<400> SEQUENCE: 55
caagcagaag acggcatacg agatggaatc tcgctcaccg aagtgggatt cctgctgtca    60
gttaa                                                                65

<210> SEQ ID NO 56
<211> LENGTH: 65
<212> TYPE: DNA
<213> ORGANISM: Artificial Sequence
<220> FEATURE:
<223> OTHER INFORMATION: LIB_IL_v2_index D705

<400> SEQUENCE: 56
caagcagaag acggcatacg agatttctga atgctcaccg aagtgggatt cctgctgtca    60
gttaa                                                                65

<210> SEQ ID NO 57
<211> LENGTH: 65
<212> TYPE: DNA
<213> ORGANISM: Artificial Sequence
<220> FEATURE:
<223> OTHER INFORMATION: LIB_IL_v2_index D706

<400> SEQUENCE: 57
caagcagaag acggcatacg agatacgaat tcgctcaccg aagtgggatt cctgctgtca    60
gttaa                                                                65

<210> SEQ ID NO 58
<211> LENGTH: 65
<212> TYPE: DNA
<213> ORGANISM: Artificial Sequence
<220> FEATURE:
<223> OTHER INFORMATION: LIB_IL_v2_index D707

<400> SEQUENCE: 58
caagcagaag acggcatacg agatagcttc aggctcaccg aagtgggatt cctgctgtca    60
gttaa                                                                65
```

<210> SEQ ID NO 59
<211> LENGTH: 65
<212> TYPE: DNA
<213> ORGANISM: Artificial Sequence
<220> FEATURE:
<223> OTHER INFORMATION: LIB_IL_v2_index D708

<400> SEQUENCE: 59
caagcagaag acggcatacg agatgcgcat tagctcaccg aagtgggatt cctgctgtca    60
gttaa                                                                65

<210> SEQ ID NO 60
<211> LENGTH: 65
<212> TYPE: DNA
<213> ORGANISM: Artificial Sequence
<220> FEATURE:
<223> OTHER INFORMATION: LIB_IL_v2_index D709

<400> SEQUENCE: 60
caagcagaag acggcatacg agatcatagc cggctcaccg aagtgggatt cctgctgtca    60
gttaa                                                                65

<210> SEQ ID NO 61
<211> LENGTH: 65
<212> TYPE: DNA
<213> ORGANISM: Artificial Sequence
<220> FEATURE:
<223> OTHER INFORMATION: LIB_IL_v2_index D710

<400> SEQUENCE: 61
caagcagaag acggcatacg agatttcgcg gagctcaccg aagtgggatt cctgctgtca    60
gttaa                                                                65

<210> SEQ ID NO 62
<211> LENGTH: 65
<212> TYPE: DNA
<213> ORGANISM: Artificial Sequence
<220> FEATURE:
<223> OTHER INFORMATION: LIB_IL_v2_index D711

<400> SEQUENCE: 62
caagcagaag acggcatacg agatgcgcga gagctcaccg aagtgggatt cctgctgtca    60
gttaa                                                                65

<210> SEQ ID NO 63
<211> LENGTH: 65
<212> TYPE: DNA
<213> ORGANISM: Artificial Sequence
<220> FEATURE:
<223> OTHER INFORMATION: LIB_IL_v2_index D712

<400> SEQUENCE: 63
caagcagaag acggcatacg agatctatcg ctgctcaccg aagtgggatt cctgctgtca    60
gttaa                                                                65

<210> SEQ ID NO 64
<211> LENGTH: 59
<212> TYPE: DNA
<213> ORGANISM: Artificial Sequence
<220> FEATURE:
<223> OTHER INFORMATION: MAL_IL_v2_index D701

<400> SEQUENCE: 64
caagcagaag acggcatacg agatcgagta atgtgagtga tggttgaggt agtgtggag        59

<210> SEQ ID NO 65
<211> LENGTH: 59
<212> TYPE: DNA
<213> ORGANISM: Artificial Sequence
<220> FEATURE:
<223> OTHER INFORMATION: MAL_IL_v2_index D702

<400> SEQUENCE: 65
caagcagaag acggcatacg agattctccg gagtgagtga tggttgaggt agtgtggag        59

<210> SEQ ID NO 66
<211> LENGTH: 59
<212> TYPE: DNA
<213> ORGANISM: Artificial Sequence
<220> FEATURE:
<223> OTHER INFORMATION: MAL_IL_v2_index D703

<400> SEQUENCE: 66
caagcagaag acggcatacg agataatgag cggtgagtga tggttgaggt agtgtggag        59

<210> SEQ ID NO 67
<211> LENGTH: 59
<212> TYPE: DNA
<213> ORGANISM: Artificial Sequence
<220> FEATURE:
<223> OTHER INFORMATION: MAL_IL_v2_index D704

<400> SEQUENCE: 67
caagcagaag acggcatacg agatggaatc tcgtgagtga tggttgaggt agtgtggag        59

<210> SEQ ID NO 68
<211> LENGTH: 59
<212> TYPE: DNA
<213> ORGANISM: Artificial Sequence
<220> FEATURE:
<223> OTHER INFORMATION: MAL_IL_v2_index D705

<400> SEQUENCE: 68
caagcagaag acggcatacg agatttctga atgtgagtga tggttgaggt agtgtggag        59

<210> SEQ ID NO 69
<211> LENGTH: 59
<212> TYPE: DNA
<213> ORGANISM: Artificial Sequence
<220> FEATURE:
<223> OTHER INFORMATION: MAL_IL_v2_index D706

<400> SEQUENCE: 69
caagcagaag acggcatacg agatacgaat tcgtgagtga tggttgaggt agtgtggag        59

<210> SEQ ID NO 70
<211> LENGTH: 59
<212> TYPE: DNA
<213> ORGANISM: Artificial Sequence
<220> FEATURE:
<223> OTHER INFORMATION: MAL_IL_v2_index D707

<400> SEQUENCE: 70
caagcagaag acggcatacg agatagcttc aggtgagtga tggttgaggt agtgtggag        59

<210> SEQ ID NO 71
<211> LENGTH: 59

```
<212> TYPE: DNA
<213> ORGANISM: Artificial Sequence
<220> FEATURE:
<223> OTHER INFORMATION: MAL_IL_v2_index D708

<400> SEQUENCE: 71
caagcagaag acggcatacg agatgcgcat tagtgagtga tggttgaggt agtgtggag      59

<210> SEQ ID NO 72
<211> LENGTH: 59
<212> TYPE: DNA
<213> ORGANISM: Artificial Sequence
<220> FEATURE:
<223> OTHER INFORMATION: MAL_IL_v2_index D709

<400> SEQUENCE: 72
caagcagaag acggcatacg agatcatagc cggtgagtga tggttgaggt agtgtggag      59

<210> SEQ ID NO 73
<211> LENGTH: 59
<212> TYPE: DNA
<213> ORGANISM: Artificial Sequence
<220> FEATURE:
<223> OTHER INFORMATION: MAL_IL_v2_index D710

<400> SEQUENCE: 73
caagcagaag acggcatacg agatttcgcg gagtgagtga tggttgaggt agtgtggag      59

<210> SEQ ID NO 74
<211> LENGTH: 59
<212> TYPE: DNA
<213> ORGANISM: Artificial Sequence
<220> FEATURE:
<223> OTHER INFORMATION: MAL_IL_v2_index D711

<400> SEQUENCE: 74
caagcagaag acggcatacg agatgcgcga gagtgagtga tggttgaggt agtgtggag      59

<210> SEQ ID NO 75
<211> LENGTH: 59
<212> TYPE: DNA
<213> ORGANISM: Artificial Sequence
<220> FEATURE:
<223> OTHER INFORMATION: MAL_IL_v2_index D712

<400> SEQUENCE: 75
caagcagaag acggcatacg agatctatcg ctgtgagtga tggttgaggt agtgtggag      59
```